US006645500B1

(12) United States Patent
Halkier et al.

(10) Patent No.: US 6,645,500 B1
(45) Date of Patent: Nov. 11, 2003

(54) METHOD FOR DOWN-REGULATING OSTEOPROTEGERIN LIGAND ACTIVITY

(75) Inventors: Torben Halkier, Birkerød (DK); Jesper Haaning, Birkerød (DK)

(73) Assignee: M & E Biotech A/S, Horsholm (DK)

(*) Notice: Subject to any disclaimer, the term of this patent is extended or adjusted under 35 U.S.C. 154(b) by 0 days.

(21) Appl. No.: 09/396,937

(22) Filed: Sep. 15, 1999

Related U.S. Application Data

(60) Provisional application No. 60/102,896, filed on Oct. 2, 1998.

(30) Foreign Application Priority Data

Sep. 15, 1998 (DK) .......................................... 98 01164

(51) Int. Cl.$^7$ ...................... A61K 39/00; A61K 39/295; A61K 38/18; C07K 14/51

(52) U.S. Cl. ............................... 424/185.1; 424/198.1; 424/192.1; 424/201.1; 530/350; 514/2

(58) Field of Search ........................... 514/2; 424/185.1, 424/192.1, 195.11, 201.1, 198.1; 530/350

(56) References Cited

FOREIGN PATENT DOCUMENTS

| | | |
|---|---|---|
| EP | 0427347 A1 | 11/1990 |
| WO | WO9505879 | 3/1995 |
| WO | 95/27058 | 10/1995 |
| WO | 97/20063 | 6/1997 |
| WO | WO9723614 | 7/1997 |
| WO | 98/25958 | 6/1998 |
| WO | 98/28426 | 7/1998 |
| WO | 98/46751 | 10/1998 |

OTHER PUBLICATIONS

Kuby, J. Immunology, Second Edition pp. 85–108 Freeman and Company New York 1994.*

Proc Natl Acad Sci USA 85(Aug. 1988) 5409–5413 Tam "Synthetic peptide . . . ".

Anderson et al: "A homologue of the TNF receptor and its ligand enhance T–cell growth and dendritic–cell function" Nature, vol. 390, Nov. 13, 1997, pp. 175–179.

Kong et al: "OPGL is a key regulator of osteoclastogenesis, lymphocyte development and lymph–node organogenesis" Nature, vol. 397, Jan. 28, 1999, pp. 315–323.

Riggs et al: "Proposed Standad Nomenclature for New Tumor Necrosis Factor Family Members Involved in the Regulation of Bone Resorption" Journal of Bone and Mineral Research, vol. 15, Nov. 12, 2000, pp. 2293–2296.

J. Immunology 1996, 157:4796–4804 Dalum et al. "Breaking of B Cell Tolerance Toward a Highly Conserved Self Protein".

J. Exp. Med. Vol 188 No. 5, Sep. 7, 1998, 997–1001 Fuller et al. "Trance Is Necessary and Sufficient for Osteoblast–mediated Activation of ..".

J. Cell Biology vol. 145 No. 3, May 3, 1999, 527–38 Burgess et al. "The Ligand for Osteoprotegerin (OPGL) Directly Activates Mature Osteoclasts".

Cell vol. 93, Apr. 17, 1998, 165–176 Lacey et al. "Osteoprotegerin Ligand Is a Cytokine that Regulates Osteoclast Differentiation and Activation".

Protein Expression and Purification 15 (1999), 389–400 Pedersen et al. "Removal of N–Terminal Polyhistidine Tags from Recombinant Proteins Using ".

Cell vol. 89, Apr. 18, 1997, 309–319 Simonet et al. "Osteoprotegerin: A Novel Secreted Protein Involved in the Regulation of Bone Density".

J. Biol. Chem. vol. 272 No. 40, Oct. 3, 1997, 25190–25194 Wong et al., "Trance Is a Novel Ligand of the Tumor Necrosis Factor Receptor ...".

Genes & Development 12 (1998), 1260–1268 Bucay et al. "Osteoprotegerin deficient mice develop early onset osteoporosis and arterial calcification".

Nature vol. 390, Nov. 13, 1997, 175–179 Anderson et al. "A homologue of the TNF receptor and its ligand enhance T–cell growth ..".

American Journal of Medical Genetics 34 (1989) 43–54 Marks, S. "Osteoclast Biology: Lessons from Mamalian Mutations".

* cited by examiner

*Primary Examiner*—Elizabeth Kemmerer
*Assistant Examiner*—Regina M. DeBerry
(74) *Attorney, Agent, or Firm*—Birch, Stewart, Kolasch & Birch, LLP

(57) ABSTRACT

The invention provides a novel method for down-regulating the biological activity of osteoprotegerin ligand (OPGL, TRANCE) thereby rendering possible the treatment/amelioration of diseases characterized by excessive loss of bone mass, e.g. osteoporosis. Down-regulation is effected by inducing an immune response against OPGL in an individual in need thereof. Immune responses can be raised by classical immunization with immunogenic variants of OPGL or by nucleic acid immunization where the nucleic acids encode the OPGL variant. The invention also pertains to compositions, polypeptides and nucleic acids useful in the invention, as well as to vectors and transformed host cells useful in the preparation thereof.

19 Claims, No Drawings

METHOD FOR DOWN-REGULATING OSTEOPROTEGERIN LIGAND ACTIVITY

This application claims priority on Provisional Application No. 06/102,896 filed on Oct. 2, 1998, the entire contents of which are hereby incorporated by reference.

FIELD OF THE INVENTION

The present invention relates to improvements in therapy and prevention of osteoporosis and other diseases characterized by continued loss of bone tissue. More specifically, the present invention provides a method for down-regulating osteoprotege-rin ligand (OPGL) by enabling the production of antibodies against OPGL in subjects suffering from or in danger of suffering from osteoporosis. The invention also provides for methods of producing modified OPGL useful in this method as well as for the modified OPGL as such. Also encompassed by the present invention are nucleic acid fragments encoding modified OPGL as well as vectors incorporating these nucleic acid fragments and host cells and cell lines transformed therewith. The invention also provides for a method for the identification of OPGL analogues which are useful in the method of the invention as well as for compositions comprising modified OPGL or comprising nucleic acids encoding the OPGL analogues.

FIELD OF THE INVENTION

Osteoporosis is a major and growing health problem worldwide. It affects an estimated 75 million people in the United States of America, Europe and Japan combined. Thus, it is the most common systemic bone disorder in the industrialised part of the world.

Osteoporosis affects one in four postmenopausal women and a majority of the elderly, including a substantial number of men. The cost of osteoporosis in the United States of America with 15 million affected people was estimated to be 3.8 billion USD annually in 1984. This translates by extrapolation to a worldwide cost of something in the order of at least 20 billion USD.

Osteoporosis is a systemic skeletal disease characterised by low bone mass and micro-architectural deterioration of bone tissue, with a consequent increase in bone fragility and susceptibility to fractures. Although all bones are affected, fractures of the spine, wrist and hip are typical and the most common. The risk of developing osteoporosis increases with age and is higher in women than in men. Its etiology appears to reside in the mechanisms underlying an accentuation of the normal loss of bone mass, which follows the menopause in women and occurs in all individuals with advancing age.

Peak bone mass is achieved at about 35 years of age. After reaching its peak, bone mass declines throughout life due to an imbalance in remodelling. Bones lose both mineral and organic matrix but retain their basic organisation.

Bone consists of a mineralised extracellular matrix composed of a variety of proteins and proteoglycans; the principal component being type I collagen. The mineral encrusting the extracellular matrix is hydroxyapatite $(Ca_3(PO_4)_2 \cdot Ca(OH)_2)$. Bone is continuously modelled during growth and development and remodelled throughout life in response to physical and chemical signals.

The growth, development and maintenance of bone are highly regulated processes, which at the cellular level involves the co-ordinate regulation of bone-forming cells (osteoblasts) and bone-resorbing cells (osteoclasts). The level of bone mass reflects the balance of bone formation and resorption.

Osteoblasts arise from mesenchymal stem cells and produce bone matrix during development, after bone injury, and during the normal bone remodelling that occurs throughout life. Osteoclasts differentiate from hematopoietic precursors of the monocyte-macrophage lineage and resorb bone matrix.

An imbalance of osteoblast and osteoclast functions can result in the skeletal abnormalities characterised by increased bone mass (osteopetrosis) or by decreased bone mass (osteoporosis).

Studies of osteopetrosis in mutant mice have shown that genetic defects in osteoclast development, maturation, and/or activation lead to decreased bone resorption and uniformly result in severe osteopetrosis (Marks, 1989). Nevertheless, relatively little has so far been known about the soluble factors that act physiologically to regulate osteoclast development.

Recently, however, two proteins that take part in this regulation have been described and characterized (Simonet et al., 1997; Lacey et al., 1998). These two proteins are osteoprotegerin and osteoprotegerin ligand.

Osteoprotegerin is a novel secreted member of the tumour necrosis factor receptor family. In vitro, osteoprotegerin blocks osteoclastogenesis in a dose dependent manner. Transgenic mice expressing osteoprotegerin exhibit a generalized increase in bone density (osteopetrosis) associated with a decrease in osteoclasts. Administration of recombinant osteoprotegerin produces similar effects in normal mice and protects against ovariectomy-associated bone loss in rats (Simonet et al., 1997). In addition, osteoprotegerin-deficient mice (knock out mice) while normal at birth develop early onset osteoporosis and arterial calcification (Bucay et al., 1998). These observations strongly point to the possibility that osteoprotegerin blocks the differentiation of osteoclasts, the principal if not sole bone-resorbing cell type, suggesting that it can act as a humoral regulator of bone resorption. Osteoprotegerin is the subject matter of WO 97/23614. It was hypothesized that osteoprotegerin may exert its effect by binding to and neutralising a factor that stimulates osteoclast development, thus inhibiting osteoclast maturation (Simonet et al., 1997).

Osteoprotegerin ligand (OPGL) is a novel member of the tumour necrosis factor family of cytokines that exists in both a membrane-bound and a soluble form. OPGL binds to osteoprotegerin with a binding affinity of 4 nM. In vitro, OPGL activates mature osteoclasts and modulates osteoclast formation from bone marrow precursors in the presence of CSF-1. It has also been demonstrated that OPGL binds to the surface of osteoclast progenitors in CSF-1-treated bone marrow. The receptor for OPGL on these hematopoeitic progenitor cells is, however, unknown. Recombinant soluble OPGL is a potent inducer of bone resorption in vivo (Lacey et al., 1998).

Description of OPGL

OPGL is synthesised as a type II transmembrane protein consisting of 317 amino acid residues (human, cf. SEQ ID NO: 2) or 316 amino acid residues (murine, cf. SEQ ID NOs: 4 and 6). Alignment of the two amino acid sequences show that identical amino acid residues are found at 87% of the homologous positions.

The OPGL amino acid sequence contains a short cytoplasmic domain in the N-terminus followed by the putative transmembrane region between amino acid residues 49 and 69. Based on its homology to tumour necrosis factor alpha, the extracellular part of OPGL has been suggested to be comprised by two domains: a stalk region extending from amino acid residue 70 to 157, and the active ligand moiety extending from amino acid residue 158 to the C-terminus.

The most closely related protein to OPGL appears to be the apoptosis inducing cytokine TRAIL with less that 25% identical amino acid residues. OPGL has also very recently been cloned in other contexts and was called TRANCE (Wong et al., 1997, J. Biol. Chem. 272: 25190–25194) and RANKL, respectively (Anderson et al., 1997, Nature 390: 175–179. The protein is also known as osteoclast differentiation factor (ODF).

Several N-terminal deletion variants of murine OPGL have been expressed in *E. coli* and purified. These variants consisted of amino acid residues 75–316, 128–316, 137–316, and 158–316, respectively. The three shortest variants had similar β-sheet structure based on circular dichroism studies, and all were able to bind to osteoprotegerin. More important, though, is that the three variants were active in in vitro assays (Lacey et al., 1998).

The shortest variant was studied further. Like tumour necrosis factor alpha, this variant OPGL exists as a trimer in solution and forms 3:3 complexes when incubated with osteoprotegerin. The binding affinity was found to be 4 nM. This variant induces duces significant increases in blood ionized calcium (hypercalcemia) in mice in vivo. Co-administration of osteoprotegerin significantly reduced this hypercalcemic effect of OPGL.

The longest variant (amino acid residues 75–316) of OPGL did not bind to osteoprotegerin and it did not have any biological activity.

At the time of construction of the N-terminal deletion variants the natural cleavage site in OPGL was not known. Expression of full-length OPGL in human 293 fibroblasts resulted in soluble OPGL beginning at amino residue 139 in the murine protein or at the homologous amino acid residue 140 in the human protein. These expression studies also showed that soluble OPGL resulting from expression in human cells is glycosylated. This is not surprising as both murine and human OPGL contain three potential N-glycosylation sites in the C-terminal ligand domain.

The concentrations of osteoprotegerin in blood and tissues are not known but the protein has significant biological activity at a concentration of 1 ng/ml.

Biological Activity of OPGL

OPGL is a potent osteoclast differentiation factor when combined with CSF-1. Neither of these components alone are capable able of inducing osteoclast differentiation from progenitor cells.

OPGL is a potent activator of mature osteoclast. On its own, OPGL activates mature osteoclasts to resorb bone. OPGL has not been observed to act as an osteoclast growth factor or osteoclast survival factor in these experiments.

The action of OPGL does not seem to be species restricted as murine OPGL also induced osteoclast formation in cultures of human peripheral blood mononuclear cells.

OBJECT OF THE INVENTION

The object of the present invention is to provide novel therapies against conditions characterized by excess bone resorption such as osteoporosis. A further object is to develop an autovaccine against OPGL, in order to obtain a novel treatment for osteoporosis and for other pathological disorders involving excess bone resorption.

SUMMARY OF THE INVENTION

We find that the above-referenced data suggests a pathophysiological role of OPGL. The in vivo evidence is partially circumstantial or indirect but is in our opinion convincing especially in combination with the direct evidence.

Observing that injection into mice of the recombinant C-terminal domain of OPGL results in severe hypercalcemia in our opinion points directly to a pathophysiological role.

Indirect evidence comes from the osteoprotegerin-deficient mice (knock out mice) that even though normal at birth develop early onset osteoporosis. This shows that removing a protein that binds OPGL and neutralises its effects leads to osteoporosis We conclude that the most likely reason for this is an increased osteoclast maturation and activation caused by OPGL.

Two other pieces of indirect evidence are that both mice transgenic for osteoprotegerin and mice injected with recombinant osteoprbtegerin develop osteopetrosis. This shows that unnatural high levels of a protein that binds OPGL and neutralises its effects leads to osteopetrosis. Here, we conclude that this has its reasons in a decreased osteoclast maturation and activation caused by neutralisation of OPGL.

We therefore suggest a model in which OPGL and osteoprotegerin act as positive and negative regulators of osteoclast development respectively. In other words OPGL promotes bone resorption while osteoprotegerin inhibits bone resorption.

Thus, in relation to osteoporosis OPGL could be thought of as a "pathogenic agent" which promotes the bone resorption that in the end leads to osteoporosis. Likewise osteoprotegerin can be visualised as a "therapeutic agent" which counteracts the "pathogenic agent" through neutralisation of its effects.

We hence propose to down-regulate osteoclast differentiation/maturation/formation and osteoclast activation through in vivo production of antibodies capable of neutralizing OPGL, thereby providing a safe and efficient means for treating/ameliorating and/or preventing osteoporosis and other diseases characterized by an excess rate of bone resorption compared to the rate of bone formation.

Thus, in its broadest and most general scope, the present invention relates to a method for in vivo down-regulation of osteoprotegerin ligand (OPGL) activity in an animal, including a human being, the method comprising effecting presentation to the animal's immune system of an immunologically effective amount of

- at least one OPGL polypeptide or subsequence thereof which has been formulated so that immunization of the animal with the OPGL polypeptide or subsequence thereof induces production of antibodies against the OPGL polypeptide, and/or
- at least one OPGL analogue wherein is introduced a modification in the OPGL polypeptide which has as a result that immunization of the animal with the analogue induces production of antibodies against the OPGL polypeptide.

The most attractive aspect of this approach is that e.g. osteoporosis can be controlled by periodic but not very frequent immunizations, in contrast to a therapeutic approach which involves frequent (e.g. daily) administration of osteoprotegerin or molecules having a binding affinity to OPGL analogous therewith. It is expected that 1–4 annual injections with an immunogenic composition will be sufficient to obtain the desired effect, whereas administration of osteoprotegerin or other inhibitors of OPGL activity would require daily administrations.

The invention also relates to OPGL analogues as well as to nucleic acid fragments encoding a subset of these. Also immunogenic compositions comprising the analogues or the nucleic acid fragments are part of the invention.

The invention also relates to a method of identifying analogues of OPGL as well as a method for preparing composition comprising the OPGL analogues.

Finally, the invention relates to a method treating osteoporosis and other diseases characterized in excess bone resorption, wherein is administered a non-OPGL molecule (typically an antibody) which blocks the interaction between OPGL and its receptor on osteoclast cells.

DETAILED DISCLOSURE OF THE INVENTION

Definitions

In the following a number of terms used in the present specification and claims will be defined and explained in 20 detail in order to clarify the metes and bounds of the invention.

The terms "T-lymphocyte" and "T-cell" will be used interchangeably for lymphocytes of thymic origin which are responsible for various cell mediated immune responses as well as for helper activity in the humoral immune response. Like-wise, the terms "B-lymphocyte" and "B-cell" will be used interchangeably for antibody-producing lymphocytes.

An "OPGL polypeptide" is herein intended to denote polypeptides having the amino acid sequence of the above-discussed OPGL proteins derived from humans and mice (or truncates thereof sharing a substantial amount of B-cell epitopes with intact OPGL), but also polypeptides having the amino acid sequence identical to analogues of these two proteins isolated from other species are embraced by the term. Also unglycosylated forms of OPGL which are prepared in prokaryotic system are included within the boundaries of the term as are forms having varying glycosylation patterns due to the use of e.g. yeasts or other non-mammalian eukaryotic expression systems. It should, however, be noted that when using the term "an OPGL polypeptide" it is intended that the polypeptide in question is normally non-immunogenic when presented to the animal to be treated. In other words, the OPGL polypeptide is. a self-protein or is an analogue of such a self-protein which will not normally give rise to an immune response against OPGL of the animal in question.

An "OPGL analogue" is an OPGL polypeptide which has been subjected to changes in its primary structure. Such a change can e.g. be in the form of fusion of an OPGL polypeptide to a suitable fusion partner (i.e. a change in primary structure exclusively involving C- and/or N-terminal additions of amino acid residues) and/or it can be in the form of insertions and/or deletions and/or substitutions in the OPGL polypeptide's amino acid sequence. Also encompassed by the term are derivatized OPGL molecules, cf. the discussion below of modifications of OPGL.

It should be noted that the use as a vaccine in a human of a xeno-analogue (e.g. a canine or porcine analogue) of human OPGL can be imagined to produce the desired immunity against OPGL. Such use of an xeno-analogue for immunization is also considered part of the invention.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "subsequence" means any consecutive stretch of at least 3 amino acids or, when relevant, of at least 3 nucleotides derived directly from a naturally occurring OPGL amino acid sequence or nucleic acid sequence, respectively.

The term "animal" is in the present context in general intended to denote an animal species (preferably mammalian), such as *Homo sapiens, Canis domesticus,* etc. and not just one single animal. However, the term also denotes a population of such an animal species, since it is important that the individuals immunized according to the method of the invention all harbour substantially the same OPGL allowing for immunization of the animals with the same immunogen(s). If, for instance, genetic variants of OPGL exists in different human population it may be necessary to use different immunogens in these different populations in order to be able to break the autotolerance towards OPGL in each population. It will be clear to the skilled person that an animal in the present context is a living being which has an immune system. It is preferred that the animal is a vertebrate, such as a mammal.

By the term "in vivo down-regulation of OPGL activity" is herein meant reduction in the living organism of the number of interactions between OPGL and its (unknown) receptor (or between OPGL and other possible biologically important binding partners for this molecule). The down-regulation can be obtained by means of several mechanisms: Of these, simple interference with the active site in OPGL by antibody binding is the most simple. However, it is also within the scope of the present invention that the antibody binding results in removal of OPGL by scavenger cells (such as macrophages and other phagocytic cells).

The expression "effecting presentation . . . to the immune system" is intended to denote that the animal's immune system is subjected to an immunogenic challenge in a controlled manner. As will appear from the disclosure below, such challenge of the immune system can be effected in a number of ways of which the most important are vaccination with polypeptide containing "pharmaccines" (i.e. a vaccine which is administered to treat or ameliorate ongoing disease) or nucleic acid "pharmaccin" vaccination. The important result to achieve is that immune competent cells in the animal are confronted with the antigen in an immunologically effective manner, whereas the precise mode of achieving this result is of less importance to the inventive idea underlying the present invention.

The term "immunogenically effective amount" has its usual meaning in the art, i.e. an amount of an immunogen which is capable of inducing an immune response which significantly engages pathogenic agents which share immunological features with the immunogen.

When using the expression that the OPGL has been "modified" is herein meant a chemical modification of the polypeptide which constitutes the backbone of OPGL. Such a modification can e.g. be derivatization (e.g. alkylation) of certain amino acid residues in the OPGL sequence, but as will be appreciated from the disclosure below, the preferred modifications comprise changes of the primary structure of the OPGL amino acid sequence.

When discussing "autotolerance towards OPGL" it is understood that since OPGL is a self-protein in the population to be vaccinated, normal individuals in the population do not mount an immune response against OPGL; it cannot be excluded, though, that occasional individuals in an animal population might be able to produce antibodies against native OPGL, e.g. as part of a autoimmune disorder. At any rate, an animal will normally only be autotolerant towards its own OPGL, but it cannot be excluded that OPGL analogues derived from other animal species or from a population having a different OPGL phenotype would also be tolerated by said animal.

A "foreign T-cell epitope" (or: "foreign T-lymphocyte epitope") is a peptide which is able to bind to an MHC molecule and which-stimulates T-cells in an animal species. Preferred foreign T-cell epitopes in the invention are "promiscuous" epitopes, i.e. epitopes which bind to a substantial fraction of a particular class of MHC molecules in an animal species or population. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same OPGL analogue or 2) prepare several OPGL analogues wherein each analogue has a different promiscuous epitope inserted. It should be noted also that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

A "foreign T helper lymphocyte epitope" (a foreign $T_H$ epitope) is a foreign T cell epitope which binds an MHC Class Class II molecule and can be presented on the surface of an antigen presenting cell (APC) bound to the MHC Class II molecule.

A "functional part" of a (bio)molecule is in the present context intended to mean the part of the molecule which is responsible for at least one of the biochemical or physiological effects exerted by the molecule. It is well-known in the art that many enzymes and other effector molecules have an active site which is responsible for the effects exerted by the molecule in question. Other parts of the molecule may serve a stabilizing or solubility enhancing purpose and can therefore be left out if these purposes are not of relevance in the context of a certain embodiment of the present invention. For instance it is possible to use certain cytokines as a modifying moiety in OPGL (cf. the detailed discussion below), and in such a case, the issue of stability may be irrelevant since the coupling to OPGL provides the stability necessary.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Targeting" of a molecule is in the present context intended to denote the situation where a molecule upon introduction in the animal will appear preferentially in certain tissue(s) or will be preferentially associated with certain cells or cell types. The effect can be accomplished in a number of ways including formulation of the molecule in composition facilitating targeting or by introduction in the molecule of groups which facilitates targeting. These issues will be discussed in detail below.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Preferred Embodiments of OPGL Activity Down-Regulation

It is preferred that the OPGL polypeptide used as an immunogen in the method of the invention is a modified molecule wherein at least one change is present in the OPGL amino acid sequence, since the chances of obtaining the all-important breaking of autotolerance towards OPGL is greatly facilitated that way. It should be noted that this does not exclude the possibility of using such a modified OPGL in formulations which further facilitate the breaking of autotolerance against OPGL, e.g. formulations containing adjuvants.

It has been shown (in Dalum I et al., 1996, J. Immunol. 157: 4796–4804) that potentially self-reactive B-lymphocytes recognizing self-proteins are physiologically present in normal individuals. However, in order for these B-lymphocytes to be induced to actually produce antibodies reactive with the relevant self-proteins, assistance is needed from cytokine producing T-helper lymphocytes ($T_H$-cells or $T_H$-lymphocytes). Normally mally this help is not provided because T-lymphocytes in general do not recognize T-cell epitopes derived from self-proteins when presented by antigen presenting cells (APCs). However, by providing an element of "foreignness" in a self-protein (i.e. by introducing an immunologically significant modification), T-cells recognizing the foreign element are activated upon recognizing the foreign epitope on an APC (such as, initially, a mononuclear cell). Polyclonal B-lymphocytes (which are also APCs) capable of recognising self-epitopes on the modified self-protein also internalise the antigen and subsequently presents the foreign T-cell epitope(s) thereof, and the activated T-lymphocytes subsequently provide cytokine help to these self-reactive polyclonal B-lymphocytes. Since the antibodies produced by these polyclonal B-lymphocytes are reactive with different epitopes on the modified polypeptide, including those which are also present in the native polypeptide, an antibody cross-reactive with the non-modified self-protein is induced. In conclusion, the T-lymphocytes can be led to act as if the population of polyclonal B-lymphocytes have recognised an entirely foreign antigen, whereas in fact only the inserted epitope(s) is/are foreign to the host. In this way, antibodies capable of cross-reacting with non-modified self-antigens are induced.

Several ways of modifying a peptide self-antigen in order to obtain breaking of autotolerance are known in the art. Hence, according to the invention, the modification can include that

- at least one foreign T-cell epitope is introduced, and/or
- at least one first moiety is introduced which effects targeting of the modified molecule to an antigen presenting cell (APC), and/or
- at least one second moiety is introduced which stimulates the immune system, and/or
- at least one third moiety is introduced which optimizes presentation of the modified OPGL polypeptide to the immune system.

However, all these modifications should be carried out while maintaining a substantial fraction of the original B-lympho-cyte epitopes in OPGL, since the B-lymphocyte recognition of the native molecule is thereby enhanced.

In one preferred embodiment, side groups (in the form of foreign T-cell epitopes or the above-mentioned first, second and third moieties) are covalently or non-covalently introduced This is to mean that stretches of amino acid residues derived from OPGL are derivatized without altering the primary amino acid sequence, or at least without introducing changes in the peptide bonds between the individual amino acids in the chain.

An alternative, and preferred, embodiment utilises amino acid substitution and/or deletion and/or insertion and/or addition (which may be effected by recombinant means or by means of peptide synthesis; modifications which involves longer stretches of amino acids can give rise to fusion polypeptides). One especially preferred version of this embodiment is the technique described in WO 95/05849, which discloses a method for down-regulating self-proteins by immunising with analogues of the self-proteins wherein a number of amino acid sequence(s) has been substituted with a corresponding number of amino acid sequence(s) which each comprise a foreign immunodominant T-cell epitope, while at the same time maintaining the overall tertiary structure of the self-protein in the analogue. For the purposes of the present invention, it is however sufficient if the modification (be it an insertion, addition, deletion or substitution) gives rise to a foreign T-cell epitope and at the same time preserves a substantial number of the B-cell epitopes in OPGL. However, in order to obtain maximum efficacy of the immune response induced, it is preferred that the overall tertiary structure of OPGL is maintained in the modified molecule.

The following formula describes the OPGL constructs generally covered by the invention:

$$(MOD_1)_{s1}(OPGL_{e1})_{n1}(MOD_2)_{s2}(OPGL_{e2})_{n2} \ldots (MOD_x)_{sx}(OPGL_{ex})_{nx} \quad (I)$$

where $OPGL_{e1}$–$OPGL_{ex}$ are x B-cell epitope containing subsequences of OPGL which independently are identical or non-identical and which may contain or not contain foreign side groups, x is an integer •3, n1–nx are x integers •0 (at least one is •(1), $MOD_1$–$MOD_x$ are x modifications introduced between the preserved served B-cell epitopes, and $s_1$–$s_x$ are x integers •0 (at least one is •1 if no side groups are introduced in the OPGLe sequences). Thus, given the general functional restraints on the immunogenicity of the constructs, the invention allows for all kinds of permutations of the original OPGL sequence, and all kinds of modifications therein. Thus, included in the invention are modified OPGL obtained by omission of parts of the OPGL sequence which e.g. exhibit adverse effects in vivo or omission of parts which are normally intracellular and thus could give rise to undesired immunological reactions.

Maintenance of a substantial fraction of B-cell epitopes or even the overall tertiary structure of a protein which is subjected to modification as described herein can be achieved in several ways. One is simply to prepare a polyclonal antiserum directed against OPGL (e.g. an antiserum prepared in a rabbit) and thereafter use this antiserum as a test reagent (e.g. in a competitive ELISA) against the modified proteins which are produced. Modified versions (analogues) which react to the same extent with the antiserum as does OPGL must be regarded as having the same overall tertiary structure as OPGL whereas analogues exhibiting a limited (but still significant and specific) reactivity with such an antiserum are regarded as having maintained a substantial fraction of the original B-cell epitopes.

Alternatively, a selection of monoclonal antibodies reactive with distinct epitopes on OPGL can be prepared and used as a test panel. This approach has the advantage of allowing 1) an epitope mapping of OPGL and 2) a mapping of the epitopes which are maintained in the analogues prepared.

Of course, a third approach would be to resolve the 3-dimensional structure of OPGL or of a biologically active truncate thereof (cf. above) and compare this to the resolved three-dimensional structure of the analogues prepared. Three-dimensional structure can be resolved by the aid of x-ray diffraction studies and NMR-spectroscopy. Further information relating to the tertiary structure can to some extent be obtained from circular dichroism studies which have the advantage of merely requiring the polypeptide in pure form (whereas X-ray diffraction requires the provision of crystallized polypeptide and NMR requires the provision of isotopic variants of the polypeptide) in order to provide useful information about the tertiary structure of a given molecule. However, ultimately x-ray diffraction and/or NMR are necessary to obtain conclusive data since circular dichroism can only provide indirect evidence of correct 3-dimensional structure via information of secondary structure elements.

One preferred embodiment of the invention utilises multiple presentations of B-lymphocyte epitopes of OPGL (i.e. formula I wherein at least one B-cell epitope is present in two positions). This effect can be achieved in various ways, e.g. by simply preparing fusion polypeptides comprising the structure $(OPGL)_m$, where m is an integer •2 and then introduce the modifications discussed herein in at least one of the OPGL sequences. It is preferred that the modifications introduced includes at least one duplication of a B-lymphocyte epitope and/or the introduction of a hapten.

As mentioned above, the introduction of a foreign T-cell epitope can be accomplished by introduction of at least one amino acid insertion, addition, deletion, or substitution. Of course, the normal situation will be the introduction of more than one change in the amino acid sequence (e.g. insertion of or substition by a complete T-cell epitope) but the important goal to reach is that the OPGL analogue, when processed by an antigen presenting cell (APC), will give rise to such a foreign immunodominant T-cell epitope being presented in context of an MCH Class II molecule on the surface of the APC. Thus, if the OPGL amino acid sequence in appropriate positions comprises a number of amino acid residues which can also be found in a foreign $T_H$ epitope then the introduction of a foreign $T_H$ epitope can be accomplished by providing the remaining amino acids of the foreign epitope by means of amino acid insertion, addition, deletion and substitution. In other words, it is not necessary to introduce a complete $T_H$ epitope by insertion or substitution in order to fulfill the purpose of the present invention.

It is preferred that the number of amino acid insertions, deletions, substitutions or additions is at least 2, such as 3, 4, 5, 6, 7, 8, 9, 10, 11, 12, 13, 14, 15, 16, 17, 18, 19, 20, and 25 insertions, substitutions, additions or deletions. It is furthermore preferred that the number of amino acid insertions, substitutions, additions or deletions is not in excess of 150, such as at most 100, at most 90, at most 80, and at most 70. It is especially preferred that the number of substitutions, insertions, deletions, or additions does not exceed 60, and in particular the number should not exceed 50 or even 40. Most preferred is a number of not more than 30. With respect to amino acid additions, it should be noted that these, when the resulting construct is in the form of a fusion polypeptide, is often considerably higher than 150.

Preferred embodiments of the invention includes modification by introducing at least one foreign immunodominant T-cell epitope. It will be understood that the question of immune dominance of a T-cell epitope depends on the animal species in question. As used herein, the term "immunodominance" simply refers to epitopes which in the vaccinated individual/population gives rise to a significant immune response, but it is a well-known fact that a T-cell epitope which is immunodominant in one individual/population is not necessarily immunodominant in another individual of the same species, even though it may be capable of binding MHC-II molecules in the latter individual. Hence, for the purposes of the present invention, an immune dominant T-cell epitope is a T-cell epitope which will be effective in providing T-cell help when present in an antigen. Typically, immune dominant T-cell epitopes has as an inherent feature that they will substantially always be presented bound to an MHC Class II molecule, irrespective of the polypeptide wherein they appear.

Another important point is the issue of MHC restriction of T-cell epitopes. In general, naturally occurring T-cell epitopes are MHC restricted, i.e. a certain peptides constituting a T-cell epitope will only bind effectively to a subset of MHC Class II molecules. This in turn has the effect that in most cases the use of one specific T-cell epitope will result in a vaccine component which is only effective in a fraction of the population, and depending on the size of that fraction, it can be necessary to include more T-cell epitopes in the same molecule, or alternatively prepare a multi-component vaccine wherein the components are OPGL variants which are distinguished from each other by the nature of the T-cell epitope introduced.

If the MHC restriction of the T-cells used is completely unknown (for instance in a situation where the vaccinated animal has a poorly defined MHC composition), the fraction of the population covered by a specific vaccine composition can be determined by means of the following formula $$f_{\text{population}} = 1 - \prod_{i=1}^{n} (1 - p_i) \quad \text{(II)}$$

where $p_i$ is the frequency in the population of responders to the $i^{th}$ foreign T-cell epitope present in the vaccine composition, and n is the total number of foreign T-cell epitopes in the vaccine composition. Thus, a vaccine composition containing 3 foreign T-cell epitopes having response frequencies in the population of 0.8, 0.7, and 0.6, respectively, would give $$1-0.2\times0.3\times0.4=0.976$$

i.e. 97.6 percent of the population will statistically mount an MHC-II mediated response to the vaccine.

The above formula does not apply in situations where a more or less precise MHC restriction pattern of the peptides used is known. If, for instance a certain peptide only binds the human MHC-II molecules encoded by HLA-DR alleles DR1, DR3, DRS, and DR7, then the use of this peptide together with another peptide which binds the remaining MHC-II molecules encoded by HLA-DR alleles will accomplish 100% coverage in the population in question. Likewise, if the second peptide only binds DR3 and DR5, the addition of this peptide will not increase the coverage at all. If one bases the calculation of population response purely on MHC restriction of T-cell epitopes in the vaccine, the fraction of the population covered by a specific vaccine composition can be determined by means of the following formula:

$$f_{\text{population}} = 1 - \prod_{j=1}^{3} (1 - \varphi_j)^2 \quad \text{(III)}$$

wherein $\phi_j$ is the sum of frequencies in the population of allelic haplotypes encoding MHC molecules which bind any one of the T-cell epitopes in the vaccine and which belong to the $j^{th}$ of the 3 known HLA loci (DP, DR and DQ); in practice, it is first determined which MHC molecules will recognize each T-cell epitope in the vaccine and thereafter these are listed by type (DP, DR and DQ)—then, the individual frequencies of the different listed allelic haplotypes are summed for each type, thereby yielding $\phi_1$, $\phi_2$, and $\phi_3$.

It may occur that the value pi in formula II exceeds the corresponding theoretical value $\#_i$:

$$\pi_i = 1 - \prod_{j=1}^{3} (1 - v_j)^2 \quad \text{(IV)}$$

wherein $u_j$ is the sum of frequencies in the population of allelic haplotype encoding MHC molecules which bind the $i^{th}$ T-cell epitope in the vaccine and which belong to the $j^{th}$ of the 3 known HLA loci (DP, DR and DQ). This means that in $1-\pi_i$ of the population is a frequency of responders of $f_{residual\_i}=(P_i-\pi_i)/(1-\pi_i)$. Therefore, formula III can be adjusted so as to yield formula V:

$$f_{\text{population}} = 1 - \prod_{j=1}^{3} (1 - \varphi_j)^2 + \left(1 - \prod_{i=1}^{n} (1 - f_{\text{residual\_i}})\right) \quad \text{(V)}$$

where the term $1-f_{residual-i}$ is set to zero if negative. It should be noted that formula V requires that all epitopes have been haplotype mapped against identical sets of haplotypes.

Therefore, when selecting T-cell epitopes to be introduced in the OPGL analogue, it is important to include all knowledge of the epitopes which is available: 1) The frequency of responders in the population to each epitope, 2) MHC restriction data, and 3) frequency in the population of the relevant haplotypes.

There exist a number of naturally occurring "promiscuous" T-cell epitopes which are active in a large proportion of individuals of an animal species or an animal population and these are preferably introduced in the vaccine thereby reducing the need for a very large number of different OPGL analogues in the same vaccine.

The promiscuous epitope can according to the invention be a naturally occurring human T-cell epitope such as epitopes from tetanus toxoid (e.g. the P2 and P30 epitopes), diphtheria toxoid, Influenza virus hemagluttinin (HA), and P. falciparum CS antigen.

Over the years a number of other promiscuous T-cell epitopes have been identified. Especially peptides capable of binding a large proportion of HLA-DR molecules encoded by the different HLA-DR alleles have been identified and these are all possible T-cell epitopes to be introduced in the OPGL-analogues used according to the present invention. Cf. also the epitopes discussed in the following references which are hereby all incorporated by reference herein: WO 98/23635 (Frazer IH et al., assigned to The University of Queensland); Southwood S et. al, 1998, J. Immunol. 160: 3363–3373; Sinigaglia F et al., 1988, Nature 336: 778–780;

Chicz RM et al., 1993, J. Exp. Med 178: 27–47; Hammer J et al., 1993, Cell 74: 197–203; and Falk K et al., 1994, Immunogenetics 39: 230–242. The latter reference also deals with HLA-DQ and -DP ligands. All epitopes listed in these 5 references are relevant as candidate natural epitopes to be used in the present invention, as are epitopes which share common motifs with these.

Alternatively, the epitope can be any artificial T-cell epitope tope which is capable of binding a large proportion of MHC Class II molecues. In this context the pan DR epitope peptides ("PADRE") described in WO 95/07707 and in the corresponding paper Alexander J et al., 1994, Immunity 1: 751–761 (both disclosures are incorporated by reference herein) are interesting candidates for epitopes to be used according to the present invention. It should be noted that the most effective PADRE peptides disclosed in these papers carry D-amino acids in the C- and N-termini in order to improve stability when administered. However, the present invention primarily aims at incorporating the relevant epitopes as part of the modified OPGL which should then subsequently be broken down enzymatically inside the lysosomal compartment of APCs to allow subsequent presentation in the context of an MHC-II molecule and therefore it is not expedient to incorporate D-amino acids in the epitopes used in the present invention.

One especially preferred PADRE peptide is the one having the amino acid sequence AKFVAAWTLKAAA (SEQ ID NO: 36) or an immunologically effective subsequence thereof. This, and other epitope having the same lack or MHC restriction are preferred T-cell epitopes which should be present in the OPGL analogues used an the inventive method. Such super-promisuous epitope will allow for the most simple embodiments of the invention wherein only one single modified OPGL is presented to the vaccinated animal's immune system.

As mentioned above, the modification of OPGL can also include the introduction of a first moiety which targets the modified OPGL to an APC or a B-lymphocyte. For instance, the first moiety can be a specific binding partner for a B-lymphocyte specific surface antigen or for an APC specific surface antigen Many such specific surface antigens are known in the art. For instance, the moiety can be a carbohydrate for which there is a receptor on the B-lymphocyte or the APC (e.g. mannan or mannose). Alternatively, the second moiety can be a hapten. Also an antibody fragment which specifically recognizes a surface molecule on APCs or lymphocytes can be used as a first moiety (the surface molecule can e.g. be an $FC_\gamma$receptor of macrophages and monocytes, such as $FC_\gamma$RI or, alternatively any other specific surface marker such as CD40 or CTLA-4). It should be noted that all these exemplary targeting molecules can be used as part of an adjuvant also, cf. below.

As an alternative or supplement to targeting the modified OPGL polypeptide to a certain cell type in order to achieve an enhanced immune response, it is possible to increase the level of responsiveness of the immune system by including the above-mentioned second moiety which stimulates the immune system.

Typical examples of such second moieties are cytokines, and heat-shock proteins or molecular chaperones, as well as effective parts thereof.

Suitable cytokines to be used according to the invention are those which will normally also function as adjuvants in a vaccine composition, i.e. for instance interferon γ (IFN-γ), interleukin 1 (IL-1), interleukin 2 (IL-2), interleukin 4 (IL-4)-, interleukin 6 (IL-6), interleukin 12 (IL-12), interleukin 13 (IL-13), interleukin 15 (IL-15), and granulocyte-macrophage colony stimulating factor (GM-CSF); alternatively, the functional part of the cytokine molecule may suffice as the second moiety. With respect to the use of such cytokines as adjuvant substances, cf. the discussion below.

According to the invention, suitable heat-shock proteins or molecular chaperones used as the second moiety can be HSP70, HSP90, HSC70, GRP94 (also known as. gp96, cf. Wearsch PA et al. 1998, Biochemistry 37: 5709–19), and CRT (calreticulin).

Alternatively, the second moiety can be a toxin, such as listeriolycin (LLO), lipid A and heat-labile enterotoxin. Also, a number of mycobacterial derivatives such as MDP (muramyl dipeptide), CFA (complete Freund's adjuvant) and the trehalose diesters TDM and TDE are interesting possibilities.

Also the possibility of introducing a third moiety which enhances the presentation of the modified OPGL to the immune system is an important embodiment of the invention. The art has shown several examples of this principle. For instance, it is known that the palmitoyl lipidation anchor in the *Borrelia burgdorferi* protein OspA can be utilised so as to provide self-adjuvating polypeptides (cf. e.g. WO 96/40718)—it seems that the lipidated proteins form up micelle-like structures with a core consisting of the lipidation anchor parts of the polypeptides and the remaining parts of the molecule protruding therefrom, resulting in multiple presentations of the antigenic determinants. Hence, the use of this and related approaches using different lipidation anchors (e.g. a myristyl group, a myristyl group, a farnesyl group, a geranyl-geranyl group, a GPI-anchor, and an N-acyl diglyceride group) are preferred embodiments of the invention, especially since the provision of such a lipidation anchor in a recombinantly produced protein is fairly straightforward and merely requires use of e.g. a naturally occurring signal sequence as a fusion partner for the modified OPGL polypeptide. Another possibility is use of the C3d fragment of complement factor C3 or C3 itself (cf. Dempsey et al., 1996, Science 271, 348–350 and Lou & Kohler, 998, Nature Biotechnology 16, 458–462).

An alternative embodiment of the invention which also results in the preferred presentation of multiple (e.g. at least 2) copies of the important epitopic regions of OPGL to the immune system is the covalent coupling of OPGL, subsequence or variants thereof to certain molecules. For instance, polymers can be used, e.g. carbohydrates such as dextran, cf. e.g. Lees A et al., 1994, Vaccine 12: 1160–1166; Lees A et al., 1990, J Immunol. 145: 3594–3600, but also mannose and mannan are useful alternative. Integral membrane proteins from e.g. *E. coli* and other bacteria are also useful conjugation partners. The traditional carrier molecules such as keyhole limpet hemocyanin (KLH), tetanus toxoid, diphtheria toxoid, and bovine serum albumin (BSA) are also preferred and useful conjugation partners.

Certain areas of native OPGL seems to be most suited for performimg modifications. Because of OPGL's structural relationship with TNF-α and other members of the tumour necrosis factor family, it is predicted that introductions of T-cell epitopes or other modifications in areas defined by positions 170–192, 198–218, 221–246, 256–261, or 285–316, (the amino acid numbering of SEQ ID NOs: 4, 6, and 12) will be most likely to produce the desired results. These positions refer to the murine OPGL—the corresponding positions in the human molecule are 171–193, 199–219, 222–247, 257–262, and 286–317 (the amino acid numbering of SEQ ID NO: 2).

Considerations underlying these chosen areas are a) preservation of known and predicted B-cell epitopes, b) preservation of tertiary structure etc. At any rate, as discussed above, it is fairly easy to screen a set of modified OPGL molecules which have all been subjected to introduction of a T-cell epitope in different locations.

Since the most preferred embodiments of the present invention involves down-regulation of human OPGL, it is consequently preferred that the OPGL polypeptide discussed above is a human OPGL polypeptide. In this embodiment, it is especially preferred that the human OPGL polypeptide has been modified by substituting at least one amino acid sequence in SEQ ID NO: 2 (or in a polypeptide where Cys-221 in SEQ ID NO: 2 has been substituted with serine) with at least one amino acid sequence of equal or different length and containing a foreign $T_H$ epitope The substituted amino acid residues are selected from residues 257–262, 289–303 and 222–243 in SEQ ID NO: 2. The rationale behind such constructs is discussed in detail in the examples.

Formulation of OPGL and Modified OPGL Polypepitides

When effecting presentation of the OPGL polypeptide or the modified OPGL polypeptide to an animal's immune system by means of administration thereof to the animal, the formulation of the polypeptide follows the principles generally acknowledge in the art.

Preparation of vaccines which contain peptide sequences as active ingredients is generally well understood in the art, as exemplified by U.S. Pat. No. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, buccal, sublinqual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredigent preferably 25–70%. For oral formulations, cholera toxin is an interesting formulation partner (and also a possible conjugation partner).

The polypeptides may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable table dosage ranges are of the order of several hundred microgram grams active ingredient per vaccination with a preferred range from about 0.1 μg to 2,000 μg (even though higher amounts in the 1–10 mg range are contemplated), such as in the range from about 0.5 μg to 1,000 μg, preferably in the range from 1 μg to 500 μg and especially in the range from about 10 μg to 100 μg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471- 95170-6, and also in "Vaccines: New Generation Immunological Adjuvants", 1995, Gregoriadis G et al. (eds.), Plenum Press, New York, ISBN 0-306-45283-9, both of which are hereby incorporated by reference herein.

It is especially preferred to use an adjuvant which can be demonstrated to facilitate breaking of the autotolerance to autoantigens; in fact, this is essential in cases where unmodified OPGL is used as the active ingredient in the autovaccine. Non-limiting examples of suitable adjuvants are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminium adjuvants; DNA adjuvants; γ-inulin; and an encapsulating adjuvant. In general it should be noted that the disclosures above which relate to compounds and agents useful as first, second and third moieties in the analogues also refer mutatis mutandis to their use in the adjuvant of a vaccine of the invention.

The application of adjuvants include use of agents such as aluminum hydroxide or phosphate (alum), commonly used as 0.05 to 0.1 percent solution in buffered saline, admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregration by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA is also preferred.

According to the invention DDA (dimethyldioctadecylammonium bromide) is an interesting candidate for an adjuvant as is DNA and γ-inulin, but also Freund's complete and incomplete adjuvants as well as quillaja saponins such as QuilA and QS21 are interesting as is RIBI. Further possibilities are monophosphoryl lipid A (MPL), the above mentioned C3 and C3d, and muramyl dipeptide (MDP).

Liposome formulations are also known to confer adjuvant effects, and therefore liposome adjuvants are preferred according to the invention.

Also immunostimulating complex matrix type (ISCOM® matrix) adjuvants are preferred choices according to the invention, especially since it has been shown that this type of adjuvants are capable of up-regulating MHC Class II expression by APCs. An ISCOM® matrix consists of (optionally fractionated) saponins (triterpenoids) from *Quillaja saponaria,* cholesterol, and phospholipid. When admixed with the immunogenic protein, the resulting particulate formulation is what is known as an ISCOM particle where the saponin constitutes 60–70% w/w, the cholesterol and phospholipid 10–15% w/w, and the protein 10–15% w/w. Details relating to composition and use of immunostimulating complexes can e.g. be found in the above-mentioned text-books dealing with adjuvants, but also Morein B et al., 1995, Clin. Immunother. 3: 461–475 as well as Barr IG and Mitchell GF, 1996, Immunol. and Cell Biol. 74: 8–25 (both incorporated by reference herein) provide useful instructions for the preparation of complete immunostimulating complexes.

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the $Fc_{\gamma}$receptors on monocytes/macrophages. Especially conjugates between antigen and anti-$Fc_{\gamma}$RI have been demonstrated to enhance immunogenicity for the purposes of vaccination.

Other possibilities involve the use of the targeting and immune modulating substances (i.a. cytokines) mentioned above as candidates for the first and second moieties in the modified versions of OPGL. In this connection, also synthetic inducers of cytokines like poly I:C are possibilities.

Suitable mycobacterial derivatives are selected from the group consisting of muramyl dipeptide, complete Freund's adjuvant, RIBI, and a diester of trehalose such as TDM and TDE.

Suitable immune targeting adjuvants are selected from the group consisting of CD40 ligand and CD40 antibodies or specifically binding fragments thereof (cf. the discussion above), mannose, a Fab fragment, and CTLA-4.

Suitable polymer adjuvants are selected from the group consisting of a carbohydrate such as dextran, PEG, starch, mannan, and mannose; a plastic polymer such as; and latex such as latex beads.

Yet another interesting way of modulating an immune response is to include the OPGL immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structrue and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is i.a. described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. $12^{th}$–$15^{th}$ 1998, Seascape Resort, Aptos, California".

It is expected that the vaccine should be administered 1–6 times per year, such as 1, 2, 3, 4, 5, or 6 times a year to an individual in need thereof. It has previously been shown that the memory immunity induced by the use of the preferred autovaccines according to the invention is not permanent, and therefore the immune system needs to be periodically challenged with the OPGL or modified OPGL polypeptides.

Due to genetic variation, different individuals may react with immune responses of varying strength to the same polypeptide. Therefore, the vaccine according to the invention may comprise several different polypeptides in order to increase the immune response, cf. also the discussion above concerning the choice of foreign T-cell epitope introductions. The vaccine may comprise two or more polypeptides, where all of the polypeptides are as defined above.

The vaccine may consequently comprise 3–20 different modified or unmodified polypeptides, such as 3–10 different polypeptides.

Nucleic Acid Vaccination

As an alternative to classic administration of a peptide-based vaccine, the technology of nucleic acid vaccination (also known as "nucleic acid immunisation", "genetic immunisation", and "gene immunisation") offers a number of attractive features.

First, in contrast to the traditional vaccine approach, nucleic acid vaccination does not require resource consuming large-scale production of the immunogenic agent (e.g. in the form of industrial scale fermentation of microorganisms producing modified OPGL). Furthermore, there is no need to device purification and refolding schemes for the immunogen. And finally, since nucleic acid vaccination relies on the biochemical apparatus of the vaccinated individual in order to produce the expression product of the nucleic acid introduced, the optimum posttranslational processing of the expression product is expected to occur; this is especially important in the case of autovaccination, since, as mentioned above, a significant fraction of the original OPGL B-cell epitopes should be preserved in the modified molecule, and since B-cell epitopes in principle can be constituted by parts of any (bio)molecule (e.g. carbohydrate, lipid, protein etc.). Therefore, native glycosylation and lipidation patterns of the immunogen may very well be of importance for the overall immunogenicity and this is best ensured by having the host producing the immunogen.

Hence, a preferred embodiment of the invention comprises effecting presentation of modified OPGL to the immune system by introducing nucleic acid(s) encoding the modified OPGL into the animal's cells and thereby obtaining in vivo expression by the cells of the nucleic acid(s) introduced.

In this embodiment, the introduced nucleic acid is preferably DNA which can be in the form of naked DNA, DNA formulated with charged or uncharged lipids, DNA formulated in liposomes, DNA included in a viral vector, DNA formulated with a transfection-facilitating protein or polypeptide, DNA formulated with a targeting protein or polypeptide, DNA formulated with Calcium precipitating agents, DNA coupled to an inert carrier molecule, DNA encapsulated in chitin or chitosan, and DNA formulated with an adjuvant. In this context it is noted that practically all considerations pertaining to the use of adjuvants in traditional vaccine formulation apply for the formulation of DNA vaccines. Hence, all disclosures herein which relate to use of adjuvants in the context of polypeptide based vaccines apply mutatis mutandis to their use in nucleic acid vaccination technology.

As for routes of administration and administration schemes of polypeptide based vaccines which have been detailed above, these are also applicable for the nucleic acid vaccines of the invention and all discussions above pertaining to routes of administration and administration schemes for polypeptides apply mutatis mutandis to nucleic acids. To this should be added that nucleic acid vaccines can suitably be administered intraveneously and intraarterially. Furthermore, it is well-known in the art that nucleic acid vaccines can be administered by use of a so-called gene gun, and hence also this and equivalent modes of administration are regarded as part of the present invention. Finally, also the use of a VLN in the administration of nucleic acids has been reported to yield good results, and therefore this particular mode of administration is particularly preferred.

Furthermore, the nucleic acid(s) used as an immunization agent can contain regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitope is produced as a fusion partner to the immunomodulator. Alternatively, two distinct nucleotide fragments can be used, but this is less preferred because of the advantage of ensured co-expression when having both coding regions included in the same molecule.

Accordingly, the invention also relates to a composition for inducing production of antibodies against OPGL, the composition comprising

- a nucleic acid fragment or a vector of the invention (cf. the discussion of vectors below), and
- a pharmaceutically and immunologically acceptable vehicle and/or carrier and/or adjuvant as discussed above.

Under normal circumstances, the OPGL variant-encoding nucleic acid is introduced in the form of a vector wherein expression is under control of a viral promoter. For more detailed discussion of vectors according to the invention, cf. the discussion below. Also, detailed disclosures relating to the formulation and use of nucleic acid vaccines are available, cf. Donnelly JJ et al, 1997, Annu. Rev. Immunol. 15: 617–648 and Donnelly JJ et al., 1997, Life Sciences 60: 163–172. Both of these references are incorporated by reference herein.

Live Vaccines

A third alternative for effecting presentation of modified OPGL to the immune system is the use of live vaccine technology. In live vaccination, presentation to the immune system is effected by administering, to the animal, a non-pathogenic microorganism which has been transformed with a nucleic acid fragment encoding a modified OPGL or with a vector incorporating such a nucleic acid fragment. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic Streptococcus spp., *E. coli,* Salmonella spp., *Vibrio cholerae,* Shigella, etc. Reviews dealing with preparation of state-of-the-art live vaccines can e.g. be found in Saliou P, 1995, Rev. Prat. 45: 1492–1496 and Walker PD, 1992, Vaccine 10: 977–990, both incorporated by reference herein. For details about the nucleic acid fragments and vectors used in such live vaccines, cf. the discussion below.

As an alternative to bacterial live vaccines, the nucleic acid fragment of the invention discussed below can be incorporated in a non-virulent viral vaccine vector such as a vaccinia strain or any other suitable pox virus.

Normally, the non-pathogenic microorganism or virus is administered only once to the animal, but in certain cases it may be necessary to administer the microorganism more than once in a lifetime in order to maintain protective immunity. It is even contemplated that immunization schemes as those detailed above for polypeptide vaccination will be useful when using live or virus vaccines.

Alternatively, live or virus vaccination is combined with previous or subsequent polypeptide and/or nucleic acid vaccination For instance, it is possible to effect primary immunization with a live or virus vaccine followed by subsequent booster immunizations using the polypeptide or nucleic acid approach.

The microorganism or virus can be transformed with nucleic acid(s) containing regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitopes are produced as fusion partners to the immunomodulator. Alternatively, two distinct nucleotide fragments can be used as transforming agents. Of course, having the $1^{st}$ and/or $2^{nd}$ and/or $3^{rd}$ moieties in the same reading frame can provide as an expression product, an analogue of the invention, and such an embodiment is especially preferred according to the present invention.

Use of the Method of the Invention in Disease Treatment

As will be appreciated from the discussions above, the provision of the method of the invention allows for control of diseases characterized by excessive loss of bone mass. In this context, the disease osteoporosis is the key target for the inventive method but also bone loss associated with complicated bone fractures is a feasible target for treatment/amelioration. Hence, an important embodiment of the method of the invention for down-regulating OPGL activity comprises treating and/or preventing and/or ameliorating osteoporosis or other conditions characterized by excess bone resorption, the method comprising down-regulating OPGL activity according to the method of the invention to such an extent that the rate of bone resorption is significantly decreased.

In the present context such a significant decrease in bone resorption is at least 3% compared to the pathological rate, but higher percentages are contemplated, such as at least 5%, at least 7%, at least 9%, at least 11%, at least 13%, at least 15%, and at least 17%, but even higher percentages are expected, such as at least 20%, or even at least 30%. It is especially preferred that the decrease in bone resorption results in an inversion of the balance between bone formation and bone resorption, i.e. that the rate of bone formation is brought to exceed the rate of bone resorption. Of course, this imbalance should not be maintained (since it would result in osteopetrosis), but by carefully controlling the number and immunological impact of immunizations of the individual in need thereof it is possible to obtain a balance over time which results in a net conservation of bone mass. Alternatively, if in an individual the method of the invention cannot terminate bone loss, the method of the invention can (optionally in combination with other known methods for reducing bone loss in osteoporosis patients) be used to obtain a significant reduction in bone loss, thereby prolonging the time where sufficient bone mass is present in the individual.

Methods for measuring the rate of bone resorption and bone formation are known in the art. It is by means of biochemical assays possible to gauge the rate of bone resorption by measuring the blood concentration of certain fragments of collagen type I (cf. WO 93/15107 and WO 94/14844). Alternatively, the rate of bone loss can be assessed by physical means; representative disclosures in the art of methods for assessing bone mass by non-invasive, physical methods can be found in WO 88/06862, WO 94/12855, WO 95/14431, and WO 97/00643.

Peptides. Polypeptide and Compositions of the Invention

As will be apparent from the above, the present invention is based on the concept of immunising individuals against the OPGL antigen in order to indirectly obtain a reduced osteoclast activity. The preferred way of obtaining such an immunization is to use modified versions of OPGL, thereby providing molecules which have not previously been disclosed in the art.

It is believed that the modified OPGL molecules discussed herein are inventive in their own right, and therefore an important part of the invention pertains to an OPGL analogue which is derived from an animal OPGL wherein is introduced a modification which has as a result that immunization of the animal with the analogue induces production of antibodies reacting specifically with the unmodified OPGL polypeptide. Preferably, the nature of the modification conforms with the types of modifications described above when discussing various embodiments of the method of the invention when using modified OPGL. Hence, any disclosure presented herein pertaining to modified OPGL molecules are relevant for the purpose of describing the OPGL analogues of the invention, and any such disclosures apply mutatis mutandis to the description of these analogues.

It should be noted that preferred modified OPGL molecules comprises modifications which results in a polypeptide having a sequence identity of at least 70% with OPGL or with a subsequence thereof of at least 10 amino acids in length. Higher sequence identities are preferred, e.g. at least 75% or even at least 80, 85, 90, or 95%. The sequence identity for proteins and nucleic acids can be calculated as $(N_{ref}-N_{dif})\cdot 100/N_{ref}$, wherein $N_{dif}$ is the total number of non-identical residues in the two sequences when aligned and wherein $N_{ref}$ is the number of residues in one of the sequences. Hence, the DNA sequence AGTCAGTC-will have a sequence identity of 75% with the sequence AATCAATC ($N_{dif}$=2 and $N_{ref}$=8).

The invention also pertains to compositions useful in exercising the method of the invention. Hence, the invention also relates to an immunogenic composition comprising an immunogenically effective amount of an OPGL polypeptide which is a self-protein in an animal, said OPGL polypeptide being formulated together with an immunologically acceptable adjuvant so as to break the animal's autotolerance towards the OPGL polypeptide, the composition further comprising a pharmaceutically and immunologically acceptable diluent and/or vehicle and/or carrier and/or excipient. In other words, this part of the invention pertains to the formulations of naturally occurring OPGL polypeptides which have been described in connection with embodiments of the method of the invention.

The invention also relates to an immunogenic composition comprising an immunologically effective amount of an OPGL analogue defined above, said composition further comprising a pharmaceutically and immunologically acceptable diluent and/or vehicle and/or carrier and/or excipient and optionally an adjuvant. In other words, this part of the invention concerns formulations of modified OPGL, essentially as described above. The choice of adjuvants, carriers, and vehicles is accordingly in line with what has been discussed above when referring to formulation of modified and unmodified OPGL for use in the inventive method for the down-regulation of OPGL.

The polypeptides are prepared according to methods well-known in the art. Longer polypeptides are normally prepared by means of recombinant gene technology including introduction of a nucleic acid sequence encoding the OPGL analogue into a suitable vector, transformation of a suitable host cell with the vector, expression of the nucleic acid sequence, recovery of the expression product from the host cells or their culture supernatant, and subseqeunt purification and optional further modification, e.g. refolding or derivatization.

Shorter peptides are preferably prepared by means of the well-known techniques of solid- or liquid-phase peptide synthesis. However, recent advances in this technology has rendered possible the production of full-length polypeptides and proteins by these means, and therefore it is also within the scope of the present invention to prepare the long constructs by synthetic means.

Nucleic Acid Fracments and Vectors of the Invention

It will be appreciated from the above disclosure that modified OPGL polypeptides can be prepared by means of recombinant gene technology but also by means of chemical synthesis or semisynthesis; the latter two options are especially relevant when the modification consists in coupling to protein carriers (such as KLH, diphtheria toxoid, tetanus toxoid, and BSA) and non-proteinaceous molecules such as carbohydrate polymers and of course also when the modification comprises addition of side chains or side groups to an OPGL polypeptide-derived peptide chain.

For the purpose of recombinant gene technology, and of course also for the purpose of nucleic acid immunization, nucleic acid fragments encoding modified OPGL are important chemical products. Hence, an important part of the invention pertains to a nucleic acid fragment which encodes an OPGL analogue, i.e. an OPGL derived polypeptide which either comprises the natural OPGL sequence to which has been added or inserted a fusion partner or, preferably an OPGL derived polypeptide wherein has been introduced a foreign T-cell epitope by means of insertion and/or addition, preferably by means of substitution and/or deletion. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors of the invention are capable of autonomous replication, thereby enabling high copy-numbers for the purposes of high-level expression or high-level replication for subsequent cloning.

The general outline of a vector of the invention comprises the following features in the 5'3' direction and in operable linkage: a promoter for driving expression of the nucleic acid fragment of the invention, optionally a nucleic acid sequence encoding a leader peptide enabling secretion (to the extracellular phase or, where applicable, into the periplasma) of or integration into the membrane of the polypeptide fragment ment, the nucleic acid fragment of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome. In contrast, when working with vectors to be used for effecting in vivo expression in an animal (i.e. when using the vector in DNA vaccination) it is for security reasons preferred that the vector is incapable of being integrated in the host cell genome; typically, naked DNA or non-integrating viral vectors are used, the choices of which are well-known to the person skilled in the art The vectors of the invention are used to transform host cells to produce the modified OPGL polypeptide of the invention. Such transformed cells, which are also part of the invention, can be cultured cells or cell lines used for propagation of the nucleic acid fragments and vectors of the invention, or used for recombinant production of the modified OPGL polypeptides of the invention. Alternatively, the transformed cells can be suitable live vaccine strains wherein the nucleic acid fragment (one single or multiple copies) have been inserted so as to effect secretion or integration into the bacterial membrane or cell-wall of the modified OPGL.

Preferred transformed cells of the invention are microorganisms such as bacteria (such as the species Escherichia [e.g. *E.colil*], Bacillus [e.g. *Bacillus subtilis*], Salmonella, or Mycobacterium [preferably non-pathogenic, e.g. *M. bovis* BCG]), yeasts (such as *Saccharomyces cerevisiae*), and protozoans. Alternatively, the transformed cells are derived from a multicellular organism such as a fungus, an insect cell, a plant cell, or a mammalian cell. Most preferred are cells derived from a human being, cf. the discussion of cell lines and vectors below. Recent results have shown great promise in the use of a commercially available *Drosophila melanogaster* cell line (the Schneider 2 ($S_2$)cell line and vector system available from Invitrogen) for the recombinant production of polypeptides in applicants' lab, and therefore this expression system is particularly preferred.

For the purposes of cloning and/or optimized expression it is preferred that the transformed cell is capable of replicating the nucleic acid fragment of the invention. Cells expressing the nucleic fragment are preferred useful embodiments of the invention; they can be used for small-scale or large-scale preparation of the modified OPGL or, in the case of non-pathogenic bacteria, as vaccine constituents in a live vaccine.

When producing the modified OPGL of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the modified OPGL. Preferably, this stable cell line secretes or carries the OPGL analogue of the invention, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artifical means.

In addition to prokaryotes, eukaryotic microbes, such as yeast cultures may also be used, and here the promoter should be capable of driving expression. *Saccharomyces cerevisiase,* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3- phosphate dehydrogenase, hexokinase, pyruvate decarboxylase, phosphofrutokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), and MDCK cell lines. In the present invention, an especially preferred cell line is S2 available from Invitrogen, PO Box 2312, 9704 CH Groningen, The Netherlands.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Identification of useful OPGL Analogues

It will be clear to the skilled person that not all possible variants or modifications of native OPGL will have the ability to elicit antibodies in an animal which are cross-reactive with the native form. It is, however, not difficult to set up an effective standard screen for modified OPGL molecules which fulfill the minimum requirements for immunological reactivity discussed herein. Hence, another part of the invention concerns a method for the identification of a modified OPGL polypeptide which is capable of inducing antibodies against unmodified OPGL in an animal species where the unmodified OPGL polypeptide is a (non-immunogenic) self-protein, the method comprising preparing, by means of peptide synthesis or genetic. engineering techniques, a set of mutually distinct modified OPGL polypeptides wherein amino acids have been added to, inserted in, deleted from, or substituted into the amino acid sequence of an OPGL polypeptide of the animal species thereby giving rise to amino acid sequences in the set which comprise T-cell epitopes which are foreign to the animal species, or preparing a set of nucleic acid fragments encoding the set of mutually distinct modified OPGL polypeptides, testing members of the set of modified OPGL polypeptides or nucleic acid fragments for their ability to induce production of antibodies by the animal species against the unmodified OPGL, and identifying and optionally isolating the member(s) of the set of modified OPGL polypeptides which significantly induces antibody production against unmodified OPGL in the species or identifying and optionally isolating the polypeptide expression products encoded by members of the set of nucleic acid fragments which significantly induces antibody production against unmodified OPGL in the animal species.

In this context, the "set of mutually distinct modified OPGL polypeptides" is a collection of non-identical modified OPGL polypeptides which have e.g. been selected on the basis of the criteria discussed above (e.g. in combination with studies of circular dichroism, NMR spectra, and/or x-ray diffraction patterns). The set may consist of only a few members but it is contemplated that the set may contain several hundred members.

The test of members of the set can ultimately be performed in vivo, but a number of in vitro tests can be applied which narrow down the number of modified molecules which will serve the purpose of the invention.

Since the goal of introducing the foreign T-cell epitopes is to support the B-cell response by T-cell help, a prerequisite is that T-cell proliferation is induced by the modified OPGL. T-cell proliferation can be tested by standardized proliferation assays in vitro. In short, a sample enriched for T-cells is obtained from a subject and subsequently kept in culture. The cultured T-cells are contacted with APCs of the subject which have previously taken up the modified molecule and processed it to present its T-cell epitopes. The proliferation of T-cells is monitored and compared to a suitable control (e.g. T-cells in culture contacted with APCs which have processed intact, native OPGL). Alternatively, proliferation can be measured by determining the concentration of relevant cytokines released by the T-cells in response to their recognition of foreign T-cells.

Having rendered highly probable that at least one modified OPGL of either type of set is capable of inducing antibody production against OPGL, it is possible to prepare an immunogenic composition comprising at least one modified OPGL polypeptide which is capable of inducing antibodies against unmodified OPGL in an animal species where the unmodified OPGL polypeptide is a self-protein, the method comprising admixing the member(s) of the set which significantly induces production of antibodies in the animal species which are reactive with OPGL with a pharmaceutically and immunologically acceptable carrier and/or vehicle and/or diluent and/or excipient, optionally in combination with at least one pharmaceutically and immunologically acceptable adjuvant.

The above aspects of the invention pertaining to test of polypeptide sets are conveniently carried out by initially preparing a number of mutually distinct nucleic acid sequences or vectors of the invention, inserting these into appropriate expression vectors, transforming suitable host cells with the vectors, and expressing the nucleic acid sequences of the invention. These steps can be followed by isolation of the expression products. It is preferred that the nucleic acid sequences and/or vectors are prepared by methods comprising exercise of a molecular amplification technique such as PCR or by means of nucleic acid synthesis.

Another part of the invention concerns a method for the treatment, prophylaxis or amelioration of diseases characterized by excess bone resorption in an animal, including a human being, the method comprising administering, to the animal, an effective amount of at least one substance different from osteoprotegerin which blocks the stimulatory effect of OPGL on osteoclast activity. It is presently believed that such an approach has never been suggested in the art.

The preferred embodiment of this part of the invention invovles use of an OPGL-specific antibody (poly- or monoclonal) or a specifically binding variant thereof as the substance blocking the stimulatory effect of OPGL. It is preferred that the antibody is an IgG or IgM molecule, or that the specifically binding varian is derived from IgG or IgM. The specifically binding variant of the antibody can conveniently be a Fab fragment, a $F(ab')_2$ fragment, a humanized monoclonal antibody or fragment thereof, or a di- or multimeric antibody fragment such as a diabody (a bispecific and dimeric artificial antibody-derived molecule produced by Cambridge Antibody Technology).

EXAMPLE

It has been decided to clone or synthesize cDNAs encoding murine and human OPGL in the truncated version comprising amino acid residues 158–316 in the murine case and residues 159–317 in the human case (numbers correspond to the numbering in SEQ ID NOs: 2 and 4, respectively). As these truncated versions exhibit biological activity, it is logical to direct the autoantibodies against this part of OPGL. In addition, it makes the proteins smaller and thus easier to handle.

A synthetic cDNA encoding the murine OPGL residues 158–316 has been synthesized removing sub-optimal *Eschericia coli* and *Pichia pastoris* codons from the published sequence. Additionally, an N-terminal Histidine tag, part of the cleavage site of the alpha mating factor signal sequence from *Sacharomyces cerevisiae,* and suitable restriction enzymes have been incorporated into the open reading frame (cf. SEQ ID NO: 7).

This cDNA encoding wild type murine OPGL has been cloned into a standard *Eschericia coli* expression vector (pTrc99a) using BspHI and HindIII restriction enzymes and a standard cloning vector (pBluescript KS+) using SacI and KpnI restriction enzymes (yielding SEQ ID NO: 9).

Expression in *Eschericia coli* cells resulted in approximately 30% recombinant OPGL of the total *Eschericia coli* protein. The protein has been refolded and purified using the following procedure:

1. Cells are harvested by centrifugation.
2. Cells are resuspended in phosphate buffered saline (PBS) and recentrifuged.
3. The supernatant is discarded and the cells are resuspended in three volumes (100 mM Tris[hydroxymethyl]aminomethane hydrochloride, 5 mM dithiotreitol (DTT), 0.5 M NaCl, pH 8.0).
4. The cells are added 8 μl 50 mM PMSF and 80 μl lysozyme (10 mg/ml) per gram cell and incubated at room temperature for 20 min.
5. For each gram cell pellet, 4 mg deoxychloric acid is added, and the suspension is incubated at 37° C. until it appears viscous.
6. 20 μl DNase (1 mg/ml) pr. gram cell weight is added, and $MgCl_2$ to 5 mM, and the suspension is incubated at room temperature for 30 min.
7. The suspension is sonicated on ice until the viscosity disappears.
8. After centrifugation (20000 ×g for 30 min) the pellet is resuspended in $H_2O$, recentrifuged and resuspended in 3 ml 1 M urea per gram cell weight.
9. After centrifugation (20000 ×g for 30 min) the pellet is resuspended in 1 M Guanidine hydrochloride, 100 mM Tris[hydroxymethyl]aminomethane hydrochloride, pH 7.5.
10. After centrifugation (20000 ×g for 30 min) the pellet is resuspended in 6 M Guanidine hydrochloride, 20 mM Tris[hydroxymethyl]aminomethane hydrochloride, 5% ethanol, 1% beta-mercaptoethanol, pH 8.0, and stirred at 4° C. overnight.
11. After centrifugation (40000 ×g for 1–4 hours) the supernatant is filtered and stored at −20° C.
12. The solubilized inclusion bodies are separated by gel filtration chromatography using Superdex 200 material (Pharmacia).
13. The fractions containing the recombinant OPGL are pooled and diluted to 0.1 mg/ml with 1.5M Guanidine hydrochloride, 20 mM Tris[hydroxymethyl]aminomethane hydrochloride, 1 mM DTT, pH 7.5.
14. The material is dialyzed overnight at 4° C. against 10 volumes 1.5 M Guanidine hydrochloride, 20 mM Tris[hydroxymethyl]aminomethane hydrochloride, 1 mM DTT, pH 7.5
15. The material is dialyzed overnight at 4° C. against 10 volumes 1.0 M Guanidine hydrochloride, 20 mM Tris[hydroxymethyl]aminomethane hydrochloride, 1 mM DTT, pH 7.5
16. The material is dialyzed overnight at 4° C. against 10 volumes 0,5 M Guanidine hydrochloride, 20 mM Tris[hydroxymethyl]aminomethane hydrochloride, 1 mM DTT, pH 7.5
17. The material is dialyzed overnight at 4° C. against 10 volumes 20 mM Tris[hydroxymethyl]aminomethane hydrochloride, 150 mM Arginine, 1 mM DTT, pH 7.5
18. The material is dialyzed overnight at 4° C. against 10 volumes 20 mM Tris[hydroxymethyl]aminomethane hydrochloride, 150 mM Arginine, pH 7.5
19. The refolded material is freeze dried and stored at −20° C.

The efficiency of refolding using this procedure is approximately 40%, and the purity in excess of 65%. The purification procedure and refolding process are still subject to further improvements. Immobilized refolding are under investigation, and enzymatic removal of the Histidine-tag will be performed essentially as described by Pedersen et al., 1999. The nature of the recombinant protein has been characterized and verified using SDS-PAGE, N-terminal sequencing, amino acid analysis, and mass spectrometry.

A cysteine substitution mutant of the wild type murine OPGL is under construction (wherein a cysteine corresponding to amino acid residue in SEQ ID NO: 4 is substituted with serine; cf. SEQ ID NOs: 11 and 12). This is done to eliminate potential stability problems with the purified recombinant protein. This mutated OPGL truncate will serve as basis for vaccine constructs in complete analogy with the description below which sets out from the DNA having SEQ ID NO: 9. Further, a corresponding Cys Ser mutant (where Cys-221 is substituted) of human OPGL will also be produced for the same purposes.

The vaccine molecules are initially constructed by insertion or in-substitution of either the P2 or P30 epitope from tetanus toxoid at selected positions. Other suitable immunodominant T-cell epitopes may be used at a later stage.

The selected positions for the introduction of variation are chosen based on knowledge of existing or predicted B-cell epitopes and predicted secondary structure elements of the native molecule, as well as using alignments with the existing three dimensional structures of TNFα (1a8m.pdb) and CD40 ligand (1a1y.pdb) for modelling the secondary and tertiary structure of the extracellular part of OPGL. The introduction in the murine molecule will take place in areas corresponding to amino acid residues 170–192, 198–218, 221–246, 256–261, and 285–316 (cf. the amino acid numbering in SEQ ID NO: 4), whereas the introduction in the human molecule will take place in areas corresponding to amino acid residues 171–193, 199–219, 222–247, 257–262, and 286–317.

Four variants of murine OPGL have by now been constructed and expressed recombinantly in *Eschericia coli:*

DNA Encoding mOPGL[158–316]_P30 [256–261] with an N-terminal Histidine tag (SEQ ID NO: 13)

PCR of SEQ ID NO: 9 was performed using SEQ ID NOs: 22 and 25 as primers. The resulting PCR fragment was restriction digested with SacII and KpnI and subsequently purified from an agarose gel. A second PCR using SEQ ID NO: 9 as template was performed using primer SEQ ID NO: 26 and a vector specific primer. The resulting PCR fragment was restriction digested with KpnI and HindIII. Both fragments were then ligated to SEQ ID NO: 9 in pBluescript KS+restriction digested with SacII and HindIII. To correct a single base mutation in this construct, PCR using the construct as template was performed with primers SEQ ID NOs: 33 and 29. The resulting PCR fragment was restriction digested with PstI+EcoRI, gel purified and subsequently ligated to the erroneous construct digested with PstI and EcoRI. The verified construct (SEQ ID NO: 13) was then transferred to pTrc99a using BspHI and HindIII restriction enzymes.

DNA encoding mOPGL[158–316]_P2[256–261] with an N-terminal Histidine tag (SEQ ID NO: 15)

PCR was performed using primers SEQ ID NOs: 27 and 28 without template. The resulting PCR fragment was restriction digested with PstI and EcoRI and subsequently purified from an agarose gel. The resulting fragment was then ligated to SEQ ID NO: 9 in pBluescript KS+ restriction digested with SacII and HindIII. The verified construct (SEQ ID NO: 15) was subsequently transferred to pTrc99a using BspHI and HindIII restriction enzymes DNA encoding mOPGL[158–316]_P2[288–302] with an N-terminal Histidine tag (SEQ ID NO: 17)

PCR of SEQ ID NO: 9 was performed using primers SEQ ID NOs: 22 and 29. The resulting PCR fragment was restriction digested with Psti and BstBI and subsequently purified from an agarose gel. A second PCR using SEQ ID NO: 9 as template was performed using primer SEQ ID NO: 30 and a vector specific primer. The resulting PCR fragment was restriction digested with BstBI and KpnI and subsequently gel purified. Both fragments were then ligated to SEQ ID NO: 9 in pBluescript KS+restriction digested with PstI and KpnI. The verified construct (SEQ ID NO: 17) was then transferred to pTrc99a using BspHI and HindIII restriction enzymes.

DNA encoding mOPGL[158–316]_P30 [221–241] with an N-terminal Histidine tag (SEQ ID NO: 19)

PCR of SEQ ID NO: 9 was performed using primers SEQ ID NOs: 22 and 23. The resulting PCR fragment was restriction digested with SacII and KpnI and subsequently purified from an agarose gel. A second PCR using SEQ ID NO: 9 as template was performed using primer SEQ ID NOs: 24 and 31. The PCR fragment was restriction digested with KpnI and EcoRI and subsequently gel purified. Both fragments were then ligated to SEQ ID NO: 9 in pBluescript KS+restriction digested with SacII and EcoRI. The verified construct (SEQ ID NO: 19) was then transferred to pTrc99a using BspHI and HindIII restriction enzymes.

Expression of these truncated variants of OPGL have taken place in *E. coli* yielding over 20% of total protein for all variants. A further development of the above-described purification and refolding procedure for the wild type protein (SEQ ID NO: 9) will be performed. This procedure will serve as a basis for the development of optimal procedures for each of the variants. Immobilized refolding of the variant proteins utilizing the Histidine tag is another approach that is being pursued.

Alternatively, the variants can be directly transferred to *Pichia pastoris* expression vectors using restriction enzymes, or other yeast expression systems using PCR if glycosylation is desired. It should be noted that the glycosylation is not needed for biological activity in vivo of OPGL. It is also possible to express the truncated OPGL in human 293 fibroblasts as reported in Lacey et al. Expression in insect cells will also be considered (e.g. the Schneider 2 ($S_2$)cell line and vector system or the *Spodoptera frugiperda* (SF) cell and vector systems, both available from Invitrogen).

The purified variants will be used for antibody production in rabbits for later use as detection tools as there exist no commercially available antibodies. In addition, this material will be a very valuable tool in the biological assays needed to evaluate the autovaccine candidates. The preparation of the antibodies will be performed using standard methods known in the art.

Selecting the best autovaccine candidate is based on assessment of inhibitory activity in in vitro assays for osteoclast maturation/activation or in in vivo animal models for osteoporosis. Useful assay and model systems are described in the literature (e.g. in Lacey et al., Fuller et al., and Simonet et al.).

The activity of the recombinant proteins will be analyzed by intravenous injection of 100 μl into un-anaesthetized male Balb/C mice (0, 0.1, and 1.0 mg protein pr. kg mouse) and one hour later withdrawal of 125 μl blood from the major eye vein using capillary tubes coated with calcium saturated heparin. The calcium levels are measured using an ICA2 (Radiometer, Denmark). Purified, and refolded recombinant murine OPGL (SEQ ID NO: 9) is reactive in this assay, increasing the circulating levels of ionized calcium by up to 10%.

The autovaccine candidates will e.g. be evaluated using autovaccination and subsequent monitoring of their inhibition of the release of ionized calcium to peripheral blood upon injection of recombinant mOPGL into mice (as described by Burgess et al.).

It should be noted that as an alternative to modified OPGL, antiidiotypic antibodies directed against the idiotype of an anti-OPGL antibody will also serve as useful immunogens within the scope of the present invention. Likewise, the use of mimotypic polypeptides which can be isolated in e.g. a phage display system using anti-OPGL or osteoprotegerin as catching probe are also considered as part of the immunogens of the invention.

List of References

1. Bucay, N. et al. (1998), Genes Dev. 12, 1260–1268.
2. Lacey, D. L. et al. (1998), Cell 93, 165–176.
3. Marks, S. C., Jr. (1989), Am. J. Med. Genet. 34, 43–53.
4. Simonet, W. S. et al. (1997), Cell 89, 309–319.
5. Fuller, K. et al. (1998), J. Exp. Med. 188, 997–1001.
6. Burgess, T. L. et al. (1999), J. Cell Biol. 145, 527–538.
7. Pedersen J et al. (1999) Protein Expr. Purif. 15, 389–400.

What is claimed is:

1. A method for in vivo down-regulation of osteoprotegerin ligand (OPGL) activity in an animal, the method comprising effecting presentation to the animal's immune system of an immunogenically effective amount of at least one OPGL polypeptide or analogue thereof which has as a result that immunization of the animal with the OPGL polypeptide or analogue thereof induces production of antibodies against the animal's own OPGL polypeptide which down-regulates the animal's own OPGL activity, wherein said OPGL polypeptide or analogue thereof comprises the sequence of residues 159–317 of SEQ ID NO. 2, or the sequence of residues 159–317 of SEQ ID NO. 2 wherein at least one foreign promiscuous, immunodominant T helper lymphocyte epitope ($T_H$), is introduced in said residues 159–317.

2. The method according to claim 1, wherein is presented an OPGL polypeptide analogue.

3. The method according to claim 1, wherein said epitope is introduced by covalent or non-covalent binding to suitable chemical groups in said OPGL polypeptide or analogue thereof.

4. The method according to claim 1, wherein the epitope is introduced by amino acid substitution, deletion, insertion, addition, or any combination thereof.

5. The method according to claim 4, wherein the resulting product is a fusion polypeptide.

6. The method according to claim 4, wherein introduction of the amino acid substitution, deletion, insertion, addition, or any combination thereof results in a substantial preservation of the overall tertiary structure of OPGL.

7. The method according to claim 1, wherein the at least one epitope is selected from a natural promiscuous T-cell epitope and an artificial MHC-II binding peptide sequence.

8. The method according to claim 7, wherein the epitope is selected from a Tetanus toxoid epitope, a diphtheria toxoid epitope, an influenza virus hemagluttinin epitope, and a *P. falciparum* CS epitope.

9. The method according to claim 1 or 8, wherein said $T_H$ has been introduced in the OPGL polypeptide in any one of positions 171–193, any one of positions 199–219, any one of positions 222–247, any one of positions 257–262, and in any one of positions 286–317, the amino acid numbering conforming with that of SEQ ID NO: 2.

10. The method according to claim 9, which comprises a substitution of at least one amino acid sequence within a position defined in claim 9 with an amino acid sequence which contains a foreign $T_H$ epitope.

11. The method according to claim 10, wherein the amino acid sequence containing the foreign $T_H$ epitope substitutes amino acids in SEQ ID NO: 2 that are selected from the group consisting of residues 257–262, 289–303 and 222–243 or in a polypeptide of SEQ ID NO: 2 where a cysteine corresponding to Cys-221 in SEQ ID NO: 2 has been substituted with Ser.

12. The method according to claim 9, wherein the animal is human and the at least one foreign T helper lymphocyte epitope ($T_H$), is selected from the group consisting of P2 and P30.

13. The method according to claim 8, wherein the Tetanus toxoid epitope is P2 or P30.

14. The method according to claim 1, wherein presentation to the immune system is effected by having at least two copies of the OPGL polypeptide or analogue thereof covalently or non-covalently linked to a carrier molecule capable of effecting presentation of multiple copies of antigenic determinants.

15. The method according to claim 1, wherein the OPGL polypeptide or analogue thereof, is formulated with an adjuvant which facilitates breaking of autotolerance to autoantigens.

16. The method according to claim 1, wherein an effective amount of the OPGL polypeptide or the OPGL analogue is administered to the animal via a route selected from the group consisting of the parenteral route; the peritoneal route; the oral route; the buccal route; the sublinqual route; the epidural route; the spinal route; the anal route; and the intracranial route.

17. The method according to claim 16, wherein the effective amount is between 0.5 $\mu$g and 2,000 $\mu$g of the OPGL polypeptide or the analogue thereof.

18. The method according to claim 16, wherein the OPGL polypeptide or analogue is contained in a virtual lymph node (VLN) device.

19. The method according to claim 16, wherein the parenteral route is intradermal, subdermal, intracutaneous, subcutaneous or intramuscular.

* * * * *

SEQUENCE LISTING

```
<160> NUMBER OF SEQ ID NOS: 36

<210> SEQ ID NO 1
<211> LENGTH: 2271
<212> TYPE: DNA
<213> ORGANISM: Homo sapiens
<220> FEATURE:
<221> NAME/KEY: CDS
<222> LOCATION: (185)..(1138)

<400> SEQUENCE: 1

aagcttggta ccgagctcgg atccactact cgacccacgc gtccgcgcgc cccaggagcc      60

aaagccgggc tccaagtcgg cgccccacgt cgaggctccg ccgcagcctc cggagttggc     120

cgcagacaag aaggggaggg agcgggagag ggaggagagc tccgaagcga gagggccgag     180

cgcc atg cgc cgc gcc agc aga gac tac acc aag tac ctg cgt ggc tcg      229
     Met Arg Arg Ala Ser Arg Asp Tyr Thr Lys Tyr Leu Arg Gly Ser
       1               5                  10                  15

gag gag atg ggc ggc ggc ccc gga gcc ccg cac gag ggc ccc ctg cac      277
Glu Glu Met Gly Gly Gly Pro Gly Ala Pro His Glu Gly Pro Leu His
                20                  25                  30

gcc ccg ccg ccg cct gcg ccg cac cag ccc ccc gcc gcc tcc cgc tcc      325
Ala Pro Pro Pro Pro Ala Pro His Gln Pro Pro Ala Ala Ser Arg Ser
            35                  40                  45

atg ttc gtg gcc ctc ctg ggg ctg ggg ctg ggc cag gtt gtc tgc agc      373
Met Phe Val Ala Leu Leu Gly Leu Gly Leu Gly Gln Val Val Cys Ser
        50                  55                  60

gtc gcc ctg ttc ttc tat ttc aga gcg cag atg gat cct aat aga ata      421
Val Ala Leu Phe Phe Tyr Phe Arg Ala Gln Met Asp Pro Asn Arg Ile
    65                  70                  75

tca gaa gat ggc act cac tgc att tat aga att ttg aga ctc cat gaa      469
Ser Glu Asp Gly Thr His Cys Ile Tyr Arg Ile Leu Arg Leu His Glu
 80                  85                  90                  95

aat gca gat ttt caa gac aca act ctg gag agt caa gat aca aaa tta      517
Asn Ala Asp Phe Gln Asp Thr Thr Leu Glu Ser Gln Asp Thr Lys Leu
                100                 105                 110

ata cct gat tca tgt agg aga att aaa cag gcc ttt caa gga gct gtg      565
Ile Pro Asp Ser Cys Arg Arg Ile Lys Gln Ala Phe Gln Gly Ala Val
            115                 120                 125

caa aag gaa tta caa cat atc gtt gga tca cag cac atc aga gca gag      613
Gln Lys Glu Leu Gln His Ile Val Gly Ser Gln His Ile Arg Ala Glu
        130                 135                 140

aaa gcg atg gtg gat ggc tca tgg tta gat ctg gcc aag agg agc aag      661
Lys Ala Met Val Asp Gly Ser Trp Leu Asp Leu Ala Lys Arg Ser Lys
    145                 150                 155

ctt gaa gct cag cct ttt gct cat ctc act att aat gcc acc gac atc      709
Leu Glu Ala Gln Pro Phe Ala His Leu Thr Ile Asn Ala Thr Asp Ile
160                 165                 170                 175

cca tct ggt tcc cat aaa gtg agt ctg tcc tct tgg tac cat gat cgg      757
Pro Ser Gly Ser His Lys Val Ser Leu Ser Ser Trp Tyr His Asp Arg
                180                 185                 190
```

-continued

```
ggt tgg gcc aag atc tcc aac atg act ttt agc aat gga aaa cta ata      805
Gly Trp Ala Lys Ile Ser Asn Met Thr Phe Ser Asn Gly Lys Leu Ile
            195                 200                 205

gtt aat cag gat ggc ttt tat tac ctg tat gcc aac att tgc ttt cga      853
Val Asn Gln Asp Gly Phe Tyr Tyr Leu Tyr Ala Asn Ile Cys Phe Arg
        210                 215                 220

cat cat gaa act tca gga gac cta gct aca gag tat ctt caa cta atg      901
His His Glu Thr Ser Gly Asp Leu Ala Thr Glu Tyr Leu Gln Leu Met
    225                 230                 235

gtg tac gtc act aaa acc agc atc aaa atc cca agt tct cat acc ctg      949
Val Tyr Val Thr Lys Thr Ser Ile Lys Ile Pro Ser Ser His Thr Leu
240                 245                 250                 255

atg aaa gga gga agc acc aag tat tgg tca ggg aat tct gaa ttc cat      997
Met Lys Gly Gly Ser Thr Lys Tyr Trp Ser Gly Asn Ser Glu Phe His
                260                 265                 270

ttt tat tcc ata aac gtt ggt gga ttt ttt aag tta cgg tct gga gag     1045
Phe Tyr Ser Ile Asn Val Gly Gly Phe Phe Lys Leu Arg Ser Gly Glu
            275                 280                 285

gaa atc agc atc gag gtc tcc aac ccc tcc tta ctg gat ccg gat cag     1093
Glu Ile Ser Ile Glu Val Ser Asn Pro Ser Leu Leu Asp Pro Asp Gln
        290                 295                 300

gat gca aca tac ttt ggg gct ttt aaa gtt cga gat ata gat tga         1138
Asp Ala Thr Tyr Phe Gly Ala Phe Lys Val Arg Asp Ile Asp
    305                 310                 315

gccccagttt ttggagtgtt atgtatttcc tggatgtttg gaaacatttt ttaaaacaag   1198

ccaagaaaga tgtatatagg tgtgtgagac tactaagagg catggcccca acggtacacg   1258

actcagtatc catgctcttg accttgtaga gaacacgcgt atttacagcc agtgggagat   1318

gttagactca tggtgtgtta cacaatggtt tttaaatttt gtaatgaatt cctagaatta   1378

aaccagattg gagcaattac gggttgacct tatgagaaac tgcatgtggg ctatgggagg   1438

ggttggtccc tggtcatgtg ccccttcgca gctgaagtgg agagggtgtc atctagcgca   1498

attgaaggat catctgaagg ggcaaattct tttgaattgt tacatcatgc tggaacctgc   1558

aaaaaatact ttttctaatg aggagagaaa atatatgtat ttttatataa tatctaaagt   1618

tatatttcag atgtaatgtt ttctttgcaa agtattgtaa attatatttg tgctatagta   1678

tttgattcaa aatatttaaa aatgtcttgc tgttgacata tttaatgttt taaatgtaca   1738

gacatattta actggtgcac tttgtaaatt ccctggggaa aacttgcagc taaggagggg   1798

aaaaaaatgt tgtttcctaa tatcaaatgc agtatatttc ttcgttcttt ttaagttaat   1858

agattttttc agacttgtca agcctgtgca aaaaaattaa aatggatgcc ttgaataata   1918

agcaggatgt tggccaccag gtgcctttca aatttagaaa ctaattgact ttagaaagct   1978

gacattgcca aaaaggatac ataatgggcc actgaaatct gtcaagagta gttatataat   2038

tgttgaacag gtgtttttcc acaagtgccg caaattgtac cttttttttt ttttcaaaat   2098

agaaaagtta ttagtggttt atcagcaaaa aagtccaatt ttaatttagt aaatgttatc   2158

ttatactgta caataaaaac attgcctttg aatgttaatt ttttggtaca aaaataaatt   2218

tatatgaaaa aaaaaaaaaa agggcggccg ctctagaggg ccctattcta tag          2271
```

<210> SEQ ID NO 2
<211> LENGTH: 317
<212> TYPE: PRT
<213> ORGANISM: Homo sapiens

<400> SEQUENCE: 2

Met Arg Arg Ala Ser Arg Asp Tyr Thr Lys Tyr Leu Arg Gly Ser Glu

-continued

```
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315
```

<210> SEQ ID NO 3
<211> LENGTH: 951
<212> TYPE: DNA
<213> ORGANISM: Mus musculus
<220> FEATURE:
<221> NAME/KEY: CDS
<222> LOCATION: (1)..(951)
<220> FEATURE:
<221> NAME/KEY: misc_feature
<222> LOCATION: (142)..(213)
<223> OTHER INFORMATION: Transmembrane domain
<220> FEATURE:
<221> NAME/KEY: misc_feature
<222> LOCATION: (454)..(948)
<223> OTHER INFORMATION: Tumour Necrosis Factor(TNF)-like domain

<400> SEQUENCE: 3

```
atg cgc cgg gcc agc cga gac tac ggc aag tac ctg cgc agc tcg gag       48
```

-continued

```
Met Arg Arg Ala Ser Arg Asp Tyr Gly Lys Tyr Leu Arg Ser Ser Glu
  1               5                  10                  15

gag atg ggc agc ggc ccc ggc gtc cca cac gag ggt ccg ctg cac ccc       96
Glu Met Gly Ser Gly Pro Gly Val Pro His Glu Gly Pro Leu His Pro
             20                  25                  30

gcg cct tct gca ccg gct ccg gcg ccg cca ccc gcc gcc tcc cgc tcc      144
Ala Pro Ser Ala Pro Ala Pro Ala Pro Pro Pro Ala Ala Ser Arg Ser
         35                  40                  45

atg ttc ctg gcc ctc ctg ggg ctg gga ctg ggc cag gtg gtc tgc agc      192
Met Phe Leu Ala Leu Leu Gly Leu Gly Leu Gly Gln Val Val Cys Ser
     50                  55                  60

atc gct ctg ttc ctg tac ttt cga gcg cag atg gat cct aac aga ata      240
Ile Ala Leu Phe Leu Tyr Phe Arg Ala Gln Met Asp Pro Asn Arg Ile
 65                  70                  75                  80

tca gaa gac agc act cac tgc ttt tat aga atc ctg aga ctc cat gaa      288
Ser Glu Asp Ser Thr His Cys Phe Tyr Arg Ile Leu Arg Leu His Glu
                 85                  90                  95

aac gca ggt ttg cag gac tcg act ctg gag agt gaa gac aca cta cct      336
Asn Ala Gly Leu Gln Asp Ser Thr Leu Glu Ser Glu Asp Thr Leu Pro
            100                 105                 110

gac tcc tgc agg agg atg aaa caa gcc ttt cag ggg gcc gtg cag aag      384
Asp Ser Cys Arg Arg Met Lys Gln Ala Phe Gln Gly Ala Val Gln Lys
        115                 120                 125

gaa ctg caa cac att gtg ggg cca cag cgc ttc tca gga gct cca gct      432
Glu Leu Gln His Ile Val Gly Pro Gln Arg Phe Ser Gly Ala Pro Ala
    130                 135                 140

atg atg gaa ggc tca tgg ttg gat gtg gcc cag cga ggc aag cct gag      480
Met Met Glu Gly Ser Trp Leu Asp Val Ala Gln Arg Gly Lys Pro Glu
145                 150                 155                 160

gcc cag cca ttt gca cac ctc acc atc aat gct gcc agc atc cca tcg      528
Ala Gln Pro Phe Ala His Leu Thr Ile Asn Ala Ala Ser Ile Pro Ser
                165                 170                 175

ggt tcc cat aaa gtc act ctg tcc tct tgg tac cac gat cga ggc tgg      576
Gly Ser His Lys Val Thr Leu Ser Ser Trp Tyr His Asp Arg Gly Trp
            180                 185                 190

gcc aag atc tct aac atg acg tta agc aac gga aaa cta agg gtt aac      624
Ala Lys Ile Ser Asn Met Thr Leu Ser Asn Gly Lys Leu Arg Val Asn
        195                 200                 205

caa gat ggc ttc tat tac ctg tac gcc aac att tgc ttt cgg cat cat      672
Gln Asp Gly Phe Tyr Tyr Leu Tyr Ala Asn Ile Cys Phe Arg His His
    210                 215                 220

gaa aca tcg gga agc gta cct aca gac tat ctt cag ctg atg gtg tat      720
Glu Thr Ser Gly Ser Val Pro Thr Asp Tyr Leu Gln Leu Met Val Tyr
225                 230                 235                 240

gtc gtt aaa acc agc atc aaa atc cca agt tct cat aac ctg atg aaa      768
Val Val Lys Thr Ser Ile Lys Ile Pro Ser Ser His Asn Leu Met Lys
                245                 250                 255

gga ggg agc acg aaa aac tgg tcg ggc aat tct gaa ttc cac ttt tat      816
Gly Gly Ser Thr Lys Asn Trp Ser Gly Asn Ser Glu Phe His Phe Tyr
            260                 265                 270

tcc ata aat gtt ggg gga ttt ttc aag ctc cga gct ggt gaa gaa att      864
Ser Ile Asn Val Gly Gly Phe Phe Lys Leu Arg Ala Gly Glu Glu Ile
        275                 280                 285

agc att cag gtg tcc aac cct tcc ctg ctg gat ccg gat caa gat gcg      912
Ser Ile Gln Val Ser Asn Pro Ser Leu Leu Asp Pro Asp Gln Asp Ala
    290                 295                 300

acg tac ttt ggg gct ttc aaa gtt cag gac ata gac tga                  951
Thr Tyr Phe Gly Ala Phe Lys Val Gln Asp Ile Asp
305                 310                 315
```

-continued

<210> SEQ ID NO 4
<211> LENGTH: 316
<212> TYPE: PRT
<213> ORGANISM: Mus musculus

<400> SEQUENCE: 4

```
Met Arg Arg Ala Ser Arg Asp Tyr Gly Lys Tyr Leu Arg Ser Ser Glu
  1               5                  10                  15

Glu Met Gly Ser Gly Pro Gly Val Pro His Glu Gly Pro Leu His Pro
             20                  25                  30

Ala Pro Ser Ala Pro Ala Pro Ala Pro Pro Pro Ala Ala Ser Arg Ser
         35                  40                  45

Met Phe Leu Ala Leu Leu Gly Leu Gly Leu Gly Gln Val Val Cys Ser
     50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                 85                  90                  95

Asn Ala Gly Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
    130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
        195                 200                 205

Gln Asp Gly Phe Tyr Tyr Leu Tyr Ala Asn Ile Cys Phe Arg His His
    210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
        275                 280                 285

Ser Ile Gln Val Ser Asn Pro Ser Leu Leu Asp Pro Asp Gln Asp Ala
    290                 295                 300

Thr Tyr Phe Gly Ala Phe Lys Val Gln Asp Ile Asp
305                 310                 315
```

<210> SEQ ID NO 5
<211> LENGTH: 2299
<212> TYPE: DNA
<213> ORGANISM: Mus musculus
<220> FEATURE:
<221> NAME/KEY: CDS
<222> LOCATION: (170)..(1120)

<400> SEQUENCE: 5

-continued

```
gagctcggat ccactactcg acccacgcgt ccgcccacgc gtccggccag gacctctgtg     60

aaccggtcgg ggcgggggcc gcctggccgg gagtctgctc ggcggtgggt ggccgaggaa    120

gggagagaac gatcgcggag cagggcgccc gaactccggg cgccgcgcc atg cgc cgg    178
                                                       Met Arg Arg
                                                         1

gcc agc cga gac tac ggc aag tac ctg cgc agc tcg gag gag atg ggc      226
Ala Ser Arg Asp Tyr Gly Lys Tyr Leu Arg Ser Ser Glu Glu Met Gly
      5                  10                  15

agc ggc ccc ggc gtc cca cac gag ggt ccg ctg cac ccc gcg cct tct      274
Ser Gly Pro Gly Val Pro His Glu Gly Pro Leu His Pro Ala Pro Ser
 20                  25                  30                  35

gca ccg gct ccg gcg ccg cca ccc gcc gcc tcc cgc tcc atg ttc ctg      322
Ala Pro Ala Pro Ala Pro Pro Pro Ala Ala Ser Arg Ser Met Phe Leu
                 40                  45                  50

gcc ctc ctg ggg ctg gga ctg ggc cag gtg gtc tgc agc atc gct ctg      370
Ala Leu Leu Gly Leu Gly Leu Gly Gln Val Val Cys Ser Ile Ala Leu
             55                  60                  65

ttc ctg tac ttt cga gcg cag atg gat cct aac aga ata tca gaa gac      418
Phe Leu Tyr Phe Arg Ala Gln Met Asp Pro Asn Arg Ile Ser Glu Asp
         70                  75                  80

agc act cac tgc ttt tat aga atc ctg aga ctc cat gaa aac gca ggt      466
Ser Thr His Cys Phe Tyr Arg Ile Leu Arg Leu His Glu Asn Ala Gly
     85                  90                  95

ttg cag gac tcg act ctg gag agt gaa gac aca cta cct gac tcc tgc      514
Leu Gln Asp Ser Thr Leu Glu Ser Glu Asp Thr Leu Pro Asp Ser Cys
100                 105                 110                 115

agg agg atg aaa caa gcc ttt cag ggg gcc gtg cag aag gaa ctg caa      562
Arg Arg Met Lys Gln Ala Phe Gln Gly Ala Val Gln Lys Glu Leu Gln
                120                 125                 130

cac att gtg ggg cca cag cgc ttc tca gga gct cca gct atg atg gaa      610
His Ile Val Gly Pro Gln Arg Phe Ser Gly Ala Pro Ala Met Met Glu
            135                 140                 145

ggc tca tgg ttg gat gtg gcc cag cga ggc aag cct gag gcc cag cca      658
Gly Ser Trp Leu Asp Val Ala Gln Arg Gly Lys Pro Glu Ala Gln Pro
        150                 155                 160

ttt gca cac ctc acc atc aat gct gcc agc atc cca tcg ggt tcc cat      706
Phe Ala His Leu Thr Ile Asn Ala Ala Ser Ile Pro Ser Gly Ser His
    165                 170                 175

aaa gtc act ctg tcc tct tgg tac cac gat cga ggc tgg gcc aag atc      754
Lys Val Thr Leu Ser Ser Trp Tyr His Asp Arg Gly Trp Ala Lys Ile
180                 185                 190                 195

tct aac atg acg tta agc aac gga aaa cta agg gtt aac caa gat ggc      802
Ser Asn Met Thr Leu Ser Asn Gly Lys Leu Arg Val Asn Gln Asp Gly
                200                 205                 210

ttc tat tac ctg tac gcc aac att tgc ttt cgg cat cat gaa aca tcg      850
Phe Tyr Tyr Leu Tyr Ala Asn Ile Cys Phe Arg His His Glu Thr Ser
            215                 220                 225

gga agc gta cct aca gac tat ctt cag ctg atg gtg tat gtc gtt aaa      898
Gly Ser Val Pro Thr Asp Tyr Leu Gln Leu Met Val Tyr Val Val Lys
        230                 235                 240

acc agc atc aaa atc cca agt tct cat aac ctg atg aaa gga ggg agc      946
Thr Ser Ile Lys Ile Pro Ser Ser His Asn Leu Met Lys Gly Gly Ser
    245                 250                 255

acg aaa aac tgg tcg ggc aat tct gaa ttc cac ttt tat tcc ata aat      994
Thr Lys Asn Trp Ser Gly Asn Ser Glu Phe His Phe Tyr Ser Ile Asn
260                 265                 270                 275

gtt ggg gga ttt ttc aag ctc cga gct ggt gaa gaa att agc att cag     1042
Val Gly Gly Phe Phe Lys Leu Arg Ala Gly Glu Glu Ile Ser Ile Gln
                280                 285                 290
```

-continued

```
gtg tcc aac cct tcc ctg ctg gat ccg gat caa gat gcg acg tac ttt     1090
Val Ser Asn Pro Ser Leu Leu Asp Pro Asp Gln Asp Ala Thr Tyr Phe
            295                 300                 305

ggg gct ttc aaa gtt cag gac ata gac tga gactcatttc gtggaacatt       1140
Gly Ala Phe Lys Val Gln Asp Ile Asp
        310                 315

agcatggatg tcctagatgt ttggaaactt cttaaaaaat ggatgatgtc tatacatgtg   1200

taagactact aagagacatg gcccacggtg tatgaaactc acagccctct ctcttgagcc   1260

tgtacaggtt gtgtatatgt aaagtccata ggtgatgtta gattcatggt gattacacaa   1320

cggttttaca attttgtaat gatttcctag aattgaacca gattgggaga ggtattccga   1380

tgcttatgaa aaacttacac gtgagctatg gaagggggtc acagtctctg ggtctaaccc   1440

ctggacatgt gccactgaga accttgaaat taagaggatg ccatgtcatt gcaaagaaat   1500

gatagtgtga agggttaagt tcttttgaat tgttacattg cgctgggacc tgcaaataag   1560

ttcttttttt ctaatgagga gagaaaaata tatgtatttt tatataatgt ctaaagttat   1620

atttcaggtg taatgttttc tgtgcaaagt tttgtaaatt atatttgtgc tatagtattt   1680

gattcaaaat atttaaaaat gtctcactgt tgacatattt aatgttttaa atgtacagat   1740

gtatttaact ggtgcacttt gtaattcccc tgaaggtact cgtagctaag gggcagaat    1800

actgtttctg gtgaccacat gtagtttatt tctttattct ttttaactta atagagtctt   1860

cagacttgtc aaaactatgc aagcaaaata aataaataaa aataaaatga ataccttgaa   1920

taataagtag gatgttggtc accaggtgcc tttcaaattt agaagctaat tgactttagg   1980

agctgacata gccaaaaagg atacataata ggctactgaa atctgtcagg agtatttatg   2040

caattattga acaggtgtct ttttttacaa gagctacaaa ttgtaaattt tgtttctttt   2100

ttttcccata gaaaatgtac tatagtttat cagccaaaaa acaatccact ttttaattta   2160

gtgaaagtta ttttattata ctgtacaata aaagcattgt ctctgaatgt taattttttg   2220

gtacaaaaaa taaatttgta cgaaaacctg aaaaaaaaaa aaaaaaaggg cggccgctct   2280

agagggccct attctatag                                                2299


<210> SEQ ID NO 6
<211> LENGTH: 316
<212> TYPE: PRT
<213> ORGANISM: Mus musculus

<400> SEQUENCE: 6

Met Arg Arg Ala Ser Arg Asp Tyr Gly Lys Tyr Leu Arg Ser Ser Glu
  1               5                  10                  15

Glu Met Gly Ser Gly Pro Gly Val Pro His Glu Gly Pro Leu His Pro
             20                  25                  30

Ala Pro Ser Ala Pro Ala Pro Ala Pro Pro Pro Ala Ala Ser Arg Ser
         35                  40                  45

Met Phe Leu Ala Leu Leu Gly Leu Gly Leu Gly Gln Val Val Cys Ser
     50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                 85                  90                  95

Asn Ala Gly Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
```

-continued

```
        115                 120                 125

Glu Leu Gln His Ile Val Gly Pro Gln Arg Phe Ser Gly Ala Pro Ala
    130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
        195                 200                 205

Gln Asp Gly Phe Tyr Tyr Leu Tyr Ala Asn Ile Cys Phe Arg His His
    210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
        275                 280                 285

Ser Ile Gln Val Ser Asn Pro Ser Leu Leu Asp Pro Asp Gln Asp Ala
    290                 295                 300

Thr Tyr Phe Gly Ala Phe Lys Val Gln Asp Ile Asp
305                 310                 315


<210> SEQ ID NO 7
<211> LENGTH: 564
<212> TYPE: DNA
<213> ORGANISM: Artificial Sequence
<220> FEATURE:
<221> NAME/KEY: CDS
<222> LOCATION: (1)..(564)
<220> FEATURE:
<223> OTHER INFORMATION: Description of Artificial Sequence: Synthetic
      PCR product with optimum codons for E. coli and P. pastoris
      expression
<220> FEATURE:
<221> NAME/KEY: misc_binding
<222> LOCATION: (43)..(84)
<223> OTHER INFORMATION: His tag
<220> FEATURE:
<221> NAME/KEY: misc_feature
<222> LOCATION: (1)..(36)
<223> OTHER INFORMATION: C-terminal part of Saccharomyces cerevisiae
      alpha-mating factor
<220> FEATURE:
<221> NAME/KEY: misc_feature
<222> LOCATION: (85)..(561)
<223> OTHER INFORMATION: Encoding wild type murine OPGL, residues
      158-316

<400> SEQUENCE: 7

gag ctc gga tcc ctc gag aaa aga gag gct gaa gct cat gtc atg aaa       48
Glu Leu Gly Ser Leu Glu Lys Arg Glu Ala Glu Ala His Val Met Lys
  1               5                  10                  15

cac caa cac caa cat caa cat caa cat caa cat caa aaa cct gaa gct       96
His Gln His Gln His Gln His Gln His Gln His Gln Lys Pro Glu Ala
            20                  25                  30

cag cca ttc gct cat ctg acc atc aac gct gca tcg atc cct tct ggt      144
Gln Pro Phe Ala His Leu Thr Ile Asn Ala Ala Ser Ile Pro Ser Gly
        35                  40                  45
```

-continued

```
tct cat aaa gtt acc ctg tct tct tgg tat cac gac cgc ggt tgg gct      192
Ser His Lys Val Thr Leu Ser Ser Trp Tyr His Asp Arg Gly Trp Ala
     50                  55                  60

aaa atc tct aac atg acc ctg tct aac ggt aaa ctg aga gtt aac cag      240
Lys Ile Ser Asn Met Thr Leu Ser Asn Gly Lys Leu Arg Val Asn Gln
 65                  70                  75                  80

gac ggt ttc tac tac ctg tac gct aac atc tgt ttc aga cat cac gaa      288
Asp Gly Phe Tyr Tyr Leu Tyr Ala Asn Ile Cys Phe Arg His His Glu
                 85                  90                  95

acc tct ggt tct gtt cca acc gac tac ctg cag ctg atg gtt tac gtt      336
Thr Ser Gly Ser Val Pro Thr Asp Tyr Leu Gln Leu Met Val Tyr Val
            100                 105                 110

gtt aaa acc tct atc aaa atc cca tct tca cat aac ctg atg aaa ggt      384
Val Lys Thr Ser Ile Lys Ile Pro Ser Ser His Asn Leu Met Lys Gly
        115                 120                 125

ggt tct acc aaa aac tgg tct ggt aac tct gaa ttc cat ttc tac tct      432
Gly Ser Thr Lys Asn Trp Ser Gly Asn Ser Glu Phe His Phe Tyr Ser
    130                 135                 140

atc aac gtt ggt ggt ttc ttc aaa ctg aga gct ggt gaa gaa atc tct      480
Ile Asn Val Gly Gly Phe Phe Lys Leu Arg Ala Gly Glu Glu Ile Ser
145                 150                 155                 160

atc cag gtt tct aac cct tct ctg ctg gac cca gac cag gac gct acc      528
Ile Gln Val Ser Asn Pro Ser Leu Leu Asp Pro Asp Gln Asp Ala Thr
                165                 170                 175

tac ttc ggg gcc ttc aaa gtt cag gac atc gac tag                      564
Tyr Phe Gly Ala Phe Lys Val Gln Asp Ile Asp
            180                 185


<210> SEQ ID NO 8
<211> LENGTH: 187
<212> TYPE: PRT
<213> ORGANISM: Artificial Sequence
<220> FEATURE:
<223> OTHER INFORMATION: Description of Artificial Sequence: Synthetic
      PCR product with optimum codons for E. coli and P. pastoris
      expression

<400> SEQUENCE: 8

Glu Leu Gly Ser Leu Glu Lys Arg Glu Ala Glu Ala His Val Met Lys
  1               5                  10                  15

His Gln His Gln His Gln His Gln His Gln His Gln Lys Pro Glu Ala
            20                  25                  30

Gln Pro Phe Ala His Leu Thr Ile Asn Ala Ala Ser Ile Pro Ser Gly
        35                  40                  45

Ser His Lys Val Thr Leu Ser Ser Trp Tyr His Asp Arg Gly Trp Ala
     50                  55                  60

Lys Ile Ser Asn Met Thr Leu Ser Asn Gly Lys Leu Arg Val Asn Gln
 65                  70                  75                  80

Asp Gly Phe Tyr Tyr Leu Tyr Ala Asn Ile Cys Phe Arg His His Glu
                 85                  90                  95

Thr Ser Gly Ser Val Pro Thr Asp Tyr Leu Gln Leu Met Val Tyr Val
            100                 105                 110

Val Lys Thr Ser Ile Lys Ile Pro Ser Ser His Asn Leu Met Lys Gly
        115                 120                 125

Gly Ser Thr Lys Asn Trp Ser Gly Asn Ser Glu Phe His Phe Tyr Ser
    130                 135                 140

Ile Asn Val Gly Gly Phe Phe Lys Leu Arg Ala Gly Glu Glu Ile Ser
145                 150                 155                 160

Ile Gln Val Ser Asn Pro Ser Leu Leu Asp Pro Asp Gln Asp Ala Thr
```

-continued

```
                165                 170                 175

Tyr Phe Gly Ala Phe Lys Val Gln Asp Ile Asp
            180                 185


<210> SEQ ID NO 9
<211> LENGTH: 519
<212> TYPE: DNA
<213> ORGANISM: Artificial Sequence
<220> FEATURE:
<223> OTHER INFORMATION: Description of Artificial Sequence: DNA
      encoding murine OPGL, residues 158-316, fused to His tag
<220> FEATURE:
<221> NAME/KEY: CDS
<222> LOCATION: (1)..(519)
<220> FEATURE:
<221> NAME/KEY: misc_binding
<222> LOCATION: (1)..(42)
<223> OTHER INFORMATION: His tag
<220> FEATURE:
<221> NAME/KEY: misc_feature
<222> LOCATION: (43)..(519)
<223> OTHER INFORMATION: Murine OPGL, residues 158-316

<400> SEQUENCE: 9

atg aaa cac caa cac caa cat caa cat caa cat caa cat caa aaa cct       48
Met Lys His Gln His Gln His Gln His Gln His Gln His Gln Lys Pro
  1               5                  10                  15

gaa gct cag cca ttc gct cat ctg acc atc aac gct gca tcg atc cct       96
Glu Ala Gln Pro Phe Ala His Leu Thr Ile Asn Ala Ala Ser Ile Pro
             20                  25                  30

tct ggt tct cat aaa gtt acc ctg tct tct tgg tat cac gac cgc ggt      144
Ser Gly Ser His Lys Val Thr Leu Ser Ser Trp Tyr His Asp Arg Gly
         35                  40                  45

tgg gct aaa atc tct aac atg acc ctg tct aac ggt aaa ctg aga gtt      192
Trp Ala Lys Ile Ser Asn Met Thr Leu Ser Asn Gly Lys Leu Arg Val
     50                  55                  60

aac cag gac ggt ttc tac tac ctg tac gct aac atc tgt ttc aga cat      240
Asn Gln Asp Gly Phe Tyr Tyr Leu Tyr Ala Asn Ile Cys Phe Arg His
 65                  70                  75                  80

cac gaa acc tct ggt tct gtt cca acc gac tac ctg cag ctg atg gtt      288
His Glu Thr Ser Gly Ser Val Pro Thr Asp Tyr Leu Gln Leu Met Val
                 85                  90                  95

tac gtt gtt aaa acc tct atc aaa atc cca tct tca cat aac ctg atg      336
Tyr Val Val Lys Thr Ser Ile Lys Ile Pro Ser Ser His Asn Leu Met
            100                 105                 110

aaa ggt ggt tct acc aaa aac tgg tct ggt aac tct gaa ttc cat ttc      384
Lys Gly Gly Ser Thr Lys Asn Trp Ser Gly Asn Ser Glu Phe His Phe
        115                 120                 125

tac tct atc aac gtt ggt ggt ttc ttc aaa ctg aga gct ggt gaa gaa      432
Tyr Ser Ile Asn Val Gly Gly Phe Phe Lys Leu Arg Ala Gly Glu Glu
    130                 135                 140

atc tct atc cag gtt tct aac cct tct ctg ctg gac cca gac cag gac      480
Ile Ser Ile Gln Val Ser Asn Pro Ser Leu Leu Asp Pro Asp Gln Asp
145                 150                 155                 160

gct acc tac ttc ggg gcc ttc aaa gtt cag gac atc gac                  519
Ala Thr Tyr Phe Gly Ala Phe Lys Val Gln Asp Ile Asp
                165                 170


<210> SEQ ID NO 10
<211> LENGTH: 173
<212> TYPE: PRT
<213> ORGANISM: Artificial Sequence
<220> FEATURE:
<223> OTHER INFORMATION: Description of Artificial Sequence: DNA
      encoding murine OPGL, residues 158-316, fused to His tag
```

-continued

<400> SEQUENCE: 10

```
Met Lys His Gln His Gln His Gln His Gln His Gln His Gln Lys Pro
  1               5                  10                  15

Glu Ala Gln Pro Phe Ala His Leu Thr Ile Asn Ala Ala Ser Ile Pro
             20                  25                  30

Ser Gly Ser His Lys Val Thr Leu Ser Ser Trp Tyr His Asp Arg Gly
         35                  40                  45

Trp Ala Lys Ile Ser Asn Met Thr Leu Ser Asn Gly Lys Leu Arg Val
     50                  55                  60

Asn Gln Asp Gly Phe Tyr Tyr Leu Tyr Ala Asn Ile Cys Phe Arg His
 65                  70                  75                  80

His Glu Thr Ser Gly Ser Val Pro Thr Asp Tyr Leu Gln Leu Met Val
                 85                  90                  95

Tyr Val Val Lys Thr Ser Ile Lys Ile Pro Ser Ser His Asn Leu Met
            100                 105                 110

Lys Gly Gly Ser Thr Lys Asn Trp Ser Gly Asn Ser Glu Phe His Phe
        115                 120                 125

Tyr Ser Ile Asn Val Gly Gly Phe Phe Lys Leu Arg Ala Gly Glu Glu
    130                 135                 140

Ile Ser Ile Gln Val Ser Asn Pro Ser Leu Leu Asp Pro Asp Gln Asp
145                 150                 155                 160

Ala Thr Tyr Phe Gly Ala Phe Lys Val Gln Asp Ile Asp
                165                 170
```

<210> SEQ ID NO 11
<211> LENGTH: 519
<212> TYPE: DNA
<213> ORGANISM: Artificial Sequence
<220> FEATURE:
<223> OTHER INFORMATION: Description of Artificial Sequence: Fusion of murine OPGL, residues 158-316 with C to S mutation, and His tag
<220> FEATURE:
<221> NAME/KEY: CDS
<222> LOCATION: (1)..(519)
<220> FEATURE:
<221> NAME/KEY: misc_binding
<222> LOCATION: (1)..(42)
<223> OTHER INFORMATION: His tag
<220> FEATURE:
<221> NAME/KEY: misc_feature
<222> LOCATION: (43)..(228)
<223> OTHER INFORMATION: Murine OPGL, residues 158-219
<220> FEATURE:
<221> NAME/KEY: misc_feature
<222> LOCATION: (232)..(519)
<223> OTHER INFORMATION: Murine OPGL, residues 221-316
<220> FEATURE:
<221> NAME/KEY: mutation
<222> LOCATION: (229)..(231)
<223> OTHER INFORMATION: tgt (Cys) to tcc (Ser)
<220> FEATURE:

<400> SEQUENCE: 11

```
atg aaa cac caa cac caa cat caa cat caa cat caa cat caa aaa cct       48
Met Lys His Gln His Gln His Gln His Gln His Gln His Gln Lys Pro
  1               5                  10                  15

gaa gct cag cca ttc gct cat ctg acc atc aac gct gca tcg atc cct       96
Glu Ala Gln Pro Phe Ala His Leu Thr Ile Asn Ala Ala Ser Ile Pro
             20                  25                  30

tct ggt tct cat aaa gtt acc ctg tct tct tgg tat cac gac cgc ggt      144
Ser Gly Ser His Lys Val Thr Leu Ser Ser Trp Tyr His Asp Arg Gly
         35                  40                  45
```

-continued

```
tgg gct aaa atc tct aac atg acc ctg tct aac ggt aaa ctg aga gtt      192
Trp Ala Lys Ile Ser Asn Met Thr Leu Ser Asn Gly Lys Leu Arg Val
     50                  55                  60

aac cag gac ggt ttc tac tac ctg tac gct aac atc tcc ttc aga cat      240
Asn Gln Asp Gly Phe Tyr Tyr Leu Tyr Ala Asn Ile Ser Phe Arg His
 65                  70                  75                  80

cac gaa acc tct ggt tct gtt cca acc gac tac ctg cag ctg atg gtt      288
His Glu Thr Ser Gly Ser Val Pro Thr Asp Tyr Leu Gln Leu Met Val
                85                  90                  95

tac gtt gtt aaa acc tct atc aaa atc cca tct tca cat aac ctg atg      336
Tyr Val Val Lys Thr Ser Ile Lys Ile Pro Ser Ser His Asn Leu Met
            100                 105                 110

aaa ggt ggt tct acc aaa aac tgg tct ggt aac tct gaa ttc cat ttc      384
Lys Gly Gly Ser Thr Lys Asn Trp Ser Gly Asn Ser Glu Phe His Phe
        115                 120                 125

tac tct atc aac gtt ggt ggt ttc ttc aaa ctg aga gct ggt gaa gaa      432
Tyr Ser Ile Asn Val Gly Gly Phe Phe Lys Leu Arg Ala Gly Glu Glu
    130                 135                 140

atc tct atc cag gtt tct aac cct tct ctg ctg gac cca gac cag gac      480
Ile Ser Ile Gln Val Ser Asn Pro Ser Leu Leu Asp Pro Asp Gln Asp
145                 150                 155                 160

gct acc tac ttc ggg gcc ttc aaa gtt cag gac atc gac                  519
Ala Thr Tyr Phe Gly Ala Phe Lys Val Gln Asp Ile Asp
                165                 170


<210> SEQ ID NO 12
<211> LENGTH: 173
<212> TYPE: PRT
<213> ORGANISM: Artificial Sequence
<220> FEATURE:
<223> OTHER INFORMATION: Description of Artificial Sequence:  Fusion of
      murine OPGL, residues 158-316 with C to S mutation, and His tag

<400> SEQUENCE: 12

Met Lys His Gln His Gln His Gln His Gln His Gln His Gln Lys Pro
  1               5                  10                  15

Glu Ala Gln Pro Phe Ala His Leu Thr Ile Asn Ala Ala Ser Ile Pro
             20                  25                  30

Ser Gly Ser His Lys Val Thr Leu Ser Ser Trp Tyr His Asp Arg Gly
         35                  40                  45

Trp Ala Lys Ile Ser Asn Met Thr Leu Ser Asn Gly Lys Leu Arg Val
     50                  55                  60

Asn Gln Asp Gly Phe Tyr Tyr Leu Tyr Ala Asn Ile Ser Phe Arg His
 65                  70                  75                  80

His Glu Thr Ser Gly Ser Val Pro Thr Asp Tyr Leu Gln Leu Met Val
                85                  90                  95

Tyr Val Val Lys Thr Ser Ile Lys Ile Pro Ser Ser His Asn Leu Met
            100                 105                 110

Lys Gly Gly Ser Thr Lys Asn Trp Ser Gly Asn Ser Glu Phe His Phe
        115                 120                 125

Tyr Ser Ile Asn Val Gly Gly Phe Phe Lys Leu Arg Ala Gly Glu Glu
    130                 135                 140

Ile Ser Ile Gln Val Ser Asn Pro Ser Leu Leu Asp Pro Asp Gln Asp
145                 150                 155                 160

Ala Thr Tyr Phe Gly Ala Phe Lys Val Gln Asp Ile Asp
                165                 170


<210> SEQ ID NO 13
<211> LENGTH: 564
```

-continued

```
<212> TYPE: DNA
<213> ORGANISM: Artificial Sequence
<220> FEATURE:
<223> OTHER INFORMATION: Description of Artificial Sequence: Fusion of
      murine OPGL, residues 158-316 modified by introduction of tetanus
      toxoid P30 epitope, and His tag
<220> FEATURE:
<221> NAME/KEY: CDS
<222> LOCATION: (1)..(564)
<220> FEATURE:
<221> NAME/KEY: misc_binding
<222> LOCATION: (1)..(42)
<223> OTHER INFORMATION: His tag
<220> FEATURE:
<221> NAME/KEY: misc_feature
<222> LOCATION: (43)..(336)
<223> OTHER INFORMATION: Murine OPGL, residues 158-255
<220> FEATURE:
<221> NAME/KEY: misc_feature
<222> LOCATION: (337)..(399)
<223> OTHER INFORMATION: Tetanus toxoid P30 epitope
<220> FEATURE:
<221> NAME/KEY: misc_feature
<222> LOCATION: (400)..(564)
<223> OTHER INFORMATION: Murine OPGL, residues 262-316

<400> SEQUENCE: 13

atg aaa cac caa cac caa cat caa cat caa cat caa cat caa aaa cct       48
Met Lys His Gln His Gln His Gln His Gln His Gln His Gln Lys Pro
  1               5                  10                  15

gaa gct cag cca ttc gct cat ctg acc atc aac gct gca tcg atc cct       96
Glu Ala Gln Pro Phe Ala His Leu Thr Ile Asn Ala Ala Ser Ile Pro
             20                  25                  30

tct ggt tct cat aaa gtt acc ctg tct tct tgg tat cac gac cgc ggt      144
Ser Gly Ser His Lys Val Thr Leu Ser Ser Trp Tyr His Asp Arg Gly
         35                  40                  45

tgg gct aaa atc tct aac atg acc ctg tct aac ggt aaa ctg aga gtt      192
Trp Ala Lys Ile Ser Asn Met Thr Leu Ser Asn Gly Lys Leu Arg Val
     50                  55                  60

aac cag gac ggt ttc tac tac ctg tac gct aac atc tgt ttc aga cat      240
Asn Gln Asp Gly Phe Tyr Tyr Leu Tyr Ala Asn Ile Cys Phe Arg His
 65                  70                  75                  80

cac gaa acc tct ggt tct gtt cca acc gac tac ctg cag ctg atg gtt      288
His Glu Thr Ser Gly Ser Val Pro Thr Asp Tyr Leu Gln Leu Met Val
                 85                  90                  95

tac gtt gtt aaa acc tct atc aaa atc cca tct tca cat aac ctg atg      336
Tyr Val Val Lys Thr Ser Ile Lys Ile Pro Ser Ser His Asn Leu Met
            100                 105                 110

ttc aac aac ttc acc gtt tct ttc tgg ctg agg gta ccg aaa gtt tct      384
Phe Asn Asn Phe Thr Val Ser Phe Trp Leu Arg Val Pro Lys Val Ser
        115                 120                 125

gct tct cac ctg gaa aac tgg tct ggt aac tct gaa ttc cat ttc tac      432
Ala Ser His Leu Glu Asn Trp Ser Gly Asn Ser Glu Phe His Phe Tyr
    130                 135                 140

tct atc aac gtt ggt ggt ttc ttc aaa ctg aga gct ggt gaa gaa atc      480
Ser Ile Asn Val Gly Gly Phe Phe Lys Leu Arg Ala Gly Glu Glu Ile
145                 150                 155                 160

tct atc cag gtt tct aac cct tct ctg ctg gac cca gac cag gac gct      528
Ser Ile Gln Val Ser Asn Pro Ser Leu Leu Asp Pro Asp Gln Asp Ala
                165                 170                 175

acc tac ttc ggg gcc ttc aaa gtt cag gac atc gac                      564
Thr Tyr Phe Gly Ala Phe Lys Val Gln Asp Ile Asp
            180                 185


<210> SEQ ID NO 14
<211> LENGTH: 188
```

-continued

<212> TYPE: PRT
<213> ORGANISM: Artificial Sequence
<220> FEATURE:
<223> OTHER INFORMATION: Description of Artificial Sequence: Fusion of murine OPGL, residues 158-316 modified by introduction of tetanus toxoid P30 epitope, and His tag

<400> SEQUENCE: 14

```
Met Lys His Gln His Gln His Gln His Gln His Gln His Gln Lys Pro
  1               5                  10                  15

Glu Ala Gln Pro Phe Ala His Leu Thr Ile Asn Ala Ala Ser Ile Pro
             20                  25                  30

Ser Gly Ser His Lys Val Thr Leu Ser Ser Trp Tyr His Asp Arg Gly
         35                  40                  45

Trp Ala Lys Ile Ser Asn Met Thr Leu Ser Asn Gly Lys Leu Arg Val
     50                  55                  60

Asn Gln Asp Gly Phe Tyr Tyr Leu Tyr Ala Asn Ile Cys Phe Arg His
 65                  70                  75                  80

His Glu Thr Ser Gly Ser Val Pro Thr Asp Tyr Leu Gln Leu Met Val
                 85                  90                  95

Tyr Val Val Lys Thr Ser Ile Lys Ile Pro Ser Ser His Asn Leu Met
            100                 105                 110

Phe Asn Asn Phe Thr Val Ser Phe Trp Leu Arg Val Pro Lys Val Ser
        115                 120                 125

Ala Ser His Leu Glu Asn Trp Ser Gly Asn Ser Glu Phe His Phe Tyr
    130                 135                 140

Ser Ile Asn Val Gly Gly Phe Phe Lys Leu Arg Ala Gly Glu Glu Ile
145                 150                 155                 160

Ser Ile Gln Val Ser Asn Pro Ser Leu Leu Asp Pro Asp Gln Asp Ala
                165                 170                 175

Thr Tyr Phe Gly Ala Phe Lys Val Gln Asp Ile Asp
            180                 185
```

<210> SEQ ID NO 15
<211> LENGTH: 546
<212> TYPE: DNA
<213> ORGANISM: Artificial Sequence
<220> FEATURE:
<223> OTHER INFORMATION: Description of Artificial Sequence: Fusion between murine OPGL, residues 158-316 with tetanus toxoid P2 epitope introduced, and His tag
<220> FEATURE:
<221> NAME/KEY: CDS
<222> LOCATION: (1)..(546)
<220> FEATURE:
<221> NAME/KEY: misc_binding
<222> LOCATION: (1)..(42)
<223> OTHER INFORMATION: His tag
<220> FEATURE:
<221> NAME/KEY: misc_feature
<222> LOCATION: (43)..(336)
<223> OTHER INFORMATION: Murine OPGL, residues 158-255
<220> FEATURE:
<221> NAME/KEY: misc_feature
<222> LOCATION: (382)..(546)
<223> OTHER INFORMATION: Murine OPGL, residues 262-316
<220> FEATURE:
<221> NAME/KEY: misc_feature
<222> LOCATION: (337)..(381)
<223> OTHER INFORMATION: Tetanus toxoid P2 epitope

<400> SEQUENCE: 15

```
atg aaa cac caa cac caa cat caa cat caa cat caa cat caa aaa cct       48
Met Lys His Gln His Gln His Gln His Gln His Gln His Gln Lys Pro
  1               5                  10                  15
```

-continued

```
gaa gct cag cca ttc gct cat ctg acc atc aac gct gca tcg atc cct       96
Glu Ala Gln Pro Phe Ala His Leu Thr Ile Asn Ala Ala Ser Ile Pro
            20                  25                  30

tct ggt tct cat aaa gtt acc ctg tct tct tgg tat cac gac cgc ggt      144
Ser Gly Ser His Lys Val Thr Leu Ser Ser Trp Tyr His Asp Arg Gly
        35                  40                  45

tgg gct aaa atc tct aac atg acc ctg tct aac ggt aaa ctg aga gtt      192
Trp Ala Lys Ile Ser Asn Met Thr Leu Ser Asn Gly Lys Leu Arg Val
    50                  55                  60

aac cag gac ggt ttc tac tac ctg tac gct aac atc tgt ttc aga cat      240
Asn Gln Asp Gly Phe Tyr Tyr Leu Tyr Ala Asn Ile Cys Phe Arg His
 65                  70                  75                  80

cac gaa acc tct ggt tct gtt cca acc gac tac ctg cag ctg atg gtt      288
His Glu Thr Ser Gly Ser Val Pro Thr Asp Tyr Leu Gln Leu Met Val
                85                  90                  95

tac gtt gtt aaa acc cct atc aaa atc caa tct tca cat aac ctg atg      336
Tyr Val Val Lys Thr Pro Ile Lys Ile Gln Ser Ser His Asn Leu Met
            100                 105                 110

cag tac atc aaa gct aat tcg aaa ttc atc ggt atc acc gaa ctg aac      384
Gln Tyr Ile Lys Ala Asn Ser Lys Phe Ile Gly Ile Thr Glu Leu Asn
        115                 120                 125

tgg tct ggt aac tct gaa ttc cat ttc tac tct atc aac gtt ggt ggt      432
Trp Ser Gly Asn Ser Glu Phe His Phe Tyr Ser Ile Asn Val Gly Gly
    130                 135                 140

ttc ttc aaa ctg aga gct ggt gaa gaa atc tct atc cag gtt tct aac      480
Phe Phe Lys Leu Arg Ala Gly Glu Glu Ile Ser Ile Gln Val Ser Asn
145                 150                 155                 160

cct tct ctg ctg gac cca gac cag gac gct acc tac ttc ggg gcc ttc      528
Pro Ser Leu Leu Asp Pro Asp Gln Asp Ala Thr Tyr Phe Gly Ala Phe
                165                 170                 175

aaa gtt cag gac atc gac                                              546
Lys Val Gln Asp Ile Asp
            180


<210> SEQ ID NO 16
<211> LENGTH: 182
<212> TYPE: PRT
<213> ORGANISM: Artificial Sequence
<220> FEATURE:
<223> OTHER INFORMATION: Description of Artificial Sequence:  Fusion
      between murine OPGL, residues 158-316 with tetanus toxoid P2
      epitope introduced, and His tag

<400> SEQUENCE: 16

Met Lys His Gln His Gln His Gln His Gln His Gln His Gln Lys Pro
  1               5                  10                  15

Glu Ala Gln Pro Phe Ala His Leu Thr Ile Asn Ala Ala Ser Ile Pro
            20                  25                  30

Ser Gly Ser His Lys Val Thr Leu Ser Ser Trp Tyr His Asp Arg Gly
        35                  40                  45

Trp Ala Lys Ile Ser Asn Met Thr Leu Ser Asn Gly Lys Leu Arg Val
    50                  55                  60

Asn Gln Asp Gly Phe Tyr Tyr Leu Tyr Ala Asn Ile Cys Phe Arg His
 65                  70                  75                  80

His Glu Thr Ser Gly Ser Val Pro Thr Asp Tyr Leu Gln Leu Met Val
                85                  90                  95

Tyr Val Val Lys Thr Pro Ile Lys Ile Gln Ser Ser His Asn Leu Met
            100                 105                 110

Gln Tyr Ile Lys Ala Asn Ser Lys Phe Ile Gly Ile Thr Glu Leu Asn
```

-continued

```
        115                 120                 125

Trp Ser Gly Asn Ser Glu Phe His Phe Tyr Ser Ile Asn Val Gly Gly
    130                 135                 140

Phe Phe Lys Leu Arg Ala Gly Glu Glu Ile Ser Ile Gln Val Ser Asn
145                 150                 155                 160

Pro Ser Leu Leu Asp Pro Asp Gln Asp Ala Thr Tyr Phe Gly Ala Phe
                165                 170                 175

Lys Val Gln Asp Ile Asp
            180


<210> SEQ ID NO 17
<211> LENGTH: 519
<212> TYPE: DNA
<213> ORGANISM: Artificial Sequence
<220> FEATURE:
<223> OTHER INFORMATION: Description of Artificial Sequence: Fusion
      between murine OPGL, residues 158-316 with tetanus toxoid
      P2 epitope introduced, and His tag
<220> FEATURE:
<221> NAME/KEY: CDS
<222> LOCATION: (1)..(519)
<220> FEATURE:
<221> NAME/KEY: misc_binding
<222> LOCATION: (1)..(42)
<223> OTHER INFORMATION: His tag
<220> FEATURE:
<221> NAME/KEY: misc_feature
<222> LOCATION: (43)..(432)
<223> OTHER INFORMATION: Murine OPGL, residues 158-287
<220> FEATURE:
<221> NAME/KEY: misc_feature
<222> LOCATION: (478)..(519)
<223> OTHER INFORMATION: Murine OPGL, residues 303-316
<220> FEATURE:
<221> NAME/KEY: misc_feature
<222> LOCATION: (433)..(477)
<223> OTHER INFORMATION: Tetanus toxoid P2 epitope

<400> SEQUENCE: 17

atg aaa cac caa cac caa cat caa cat caa cat caa cat caa aaa cct       48
Met Lys His Gln His Gln His Gln His Gln His Gln His Gln Lys Pro
  1               5                  10                  15

gaa gct cag cca ttc gct cat ctg acc atc aac gct gca tcg atc cct       96
Glu Ala Gln Pro Phe Ala His Leu Thr Ile Asn Ala Ala Ser Ile Pro
             20                  25                  30

tct ggt tct cat aaa gtt acc ctg tct tct tgg tat cac gac cgc ggt      144
Ser Gly Ser His Lys Val Thr Leu Ser Ser Trp Tyr His Asp Arg Gly
         35                  40                  45

tgg gct aaa atc tct aac atg acc ctg tct aac ggt aaa ctg aga gtt      192
Trp Ala Lys Ile Ser Asn Met Thr Leu Ser Asn Gly Lys Leu Arg Val
     50                  55                  60

aac cag gac ggt ttc tac tac ctg tac gct aac atc tgt ttc aga cat      240
Asn Gln Asp Gly Phe Tyr Tyr Leu Tyr Ala Asn Ile Cys Phe Arg His
 65                  70                  75                  80

cac gaa acc tct ggt tct gtt cca acc gac tac ctg cag ctg atg gtt      288
His Glu Thr Ser Gly Ser Val Pro Thr Asp Tyr Leu Gln Leu Met Val
                 85                  90                  95

tac gtt gtt aaa acc tct atc aaa atc cca tct tca cat aac ctg atg      336
Tyr Val Val Lys Thr Ser Ile Lys Ile Pro Ser Ser His Asn Leu Met
            100                 105                 110

aaa ggt ggt tct acc aaa aac tgg tct ggt aac tct gaa ttc cat ttc      384
Lys Gly Gly Ser Thr Lys Asn Trp Ser Gly Asn Ser Glu Phe His Phe
        115                 120                 125

tac tct atc aac gtt ggt ggt ttc ttc aaa ctg aga gct ggt gaa gaa      432
Tyr Ser Ile Asn Val Gly Gly Phe Phe Lys Leu Arg Ala Gly Glu Glu
```

-continued

```
    130                 135                 140

cag tac atc aaa gct aat tcg aaa ttc atc ggt atc acc gaa ctg gac      480
Gln Tyr Ile Lys Ala Asn Ser Lys Phe Ile Gly Ile Thr Glu Leu Asp
145                 150                 155                 160

gct acc tac ttc ggg gcc ttc aaa gtt cag gac atc gac                  519
Ala Thr Tyr Phe Gly Ala Phe Lys Val Gln Asp Ile Asp
                165                 170


<210> SEQ ID NO 18
<211> LENGTH: 173
<212> TYPE: PRT
<213> ORGANISM: Artificial Sequence
<220> FEATURE:
<223> OTHER INFORMATION: Description of Artificial Sequence: Fusion
      between murine OPGL, residues 158-316 with tetanus toxoid
      P2 epitope introduced, and His tag

<400> SEQUENCE: 18

Met Lys His Gln His Gln His Gln His Gln His Gln His Gln Lys Pro
  1               5                  10                  15

Glu Ala Gln Pro Phe Ala His Leu Thr Ile Asn Ala Ala Ser Ile Pro
             20                  25                  30

Ser Gly Ser His Lys Val Thr Leu Ser Ser Trp Tyr His Asp Arg Gly
        35                  40                  45

Trp Ala Lys Ile Ser Asn Met Thr Leu Ser Asn Gly Lys Leu Arg Val
     50                  55                  60

Asn Gln Asp Gly Phe Tyr Tyr Leu Tyr Ala Asn Ile Cys Phe Arg His
 65                  70                  75                  80

His Glu Thr Ser Gly Ser Val Pro Thr Asp Tyr Leu Gln Leu Met Val
                 85                  90                  95

Tyr Val Val Lys Thr Ser Ile Lys Ile Pro Ser Ser His Asn Leu Met
            100                 105                 110

Lys Gly Gly Ser Thr Lys Asn Trp Ser Gly Asn Ser Glu Phe His Phe
        115                 120                 125

Tyr Ser Ile Asn Val Gly Gly Phe Phe Lys Leu Arg Ala Gly Glu Glu
    130                 135                 140

Gln Tyr Ile Lys Ala Asn Ser Lys Phe Ile Gly Ile Thr Glu Leu Asp
145                 150                 155                 160

Ala Thr Tyr Phe Gly Ala Phe Lys Val Gln Asp Ile Asp
                165                 170


<210> SEQ ID NO 19
<211> LENGTH: 519
<212> TYPE: DNA
<213> ORGANISM: Artificial Sequence
<220> FEATURE:
<223> OTHER INFORMATION: Description of Artificial Sequence: Fusion
      between murine OPGL, residues 158-316 with tetanus toxoid
      P30 epitope introduced, and His tag
<220> FEATURE:
<221> NAME/KEY: CDS
<222> LOCATION: (1)..(519)
<220> FEATURE:
<221> NAME/KEY: misc_binding
<222> LOCATION: (1)..(42)
<223> OTHER INFORMATION: His tag
<220> FEATURE:
<221> NAME/KEY: misc_feature
<222> LOCATION: (43)..(231)
<223> OTHER INFORMATION: Murine OPGL, residues 158-220
<220> FEATURE:
<221> NAME/KEY: misc_feature
<222> LOCATION: (295)..(519)
<223> OTHER INFORMATION: Murine OPGL, residues 242-316
```

-continued

```
<220> FEATURE:
<221> NAME/KEY: misc_feature
<222> LOCATION: (232)..(294)
<223> OTHER INFORMATION: Tetanus toxoid P30 epitope

<400> SEQUENCE: 19

atg aaa cac caa cac caa cat caa cat caa cat caa cat caa aaa cct       48
Met Lys His Gln His Gln His Gln His Gln His Gln His Gln Lys Pro
  1               5                  10                  15

gaa gct cag cca ttc gct cat ctg acc atc aac gct gca tcg atc cct       96
Glu Ala Gln Pro Phe Ala His Leu Thr Ile Asn Ala Ala Ser Ile Pro
             20                  25                  30

tct ggt tct cat aaa gtt acc ctg tct tct tgg tat cac gac cgc ggt      144
Ser Gly Ser His Lys Val Thr Leu Ser Ser Trp Tyr His Asp Arg Gly
         35                  40                  45

tgg gct aaa atc tct aac atg acc ctg tct aac ggt aaa ctg aga gtt      192
Trp Ala Lys Ile Ser Asn Met Thr Leu Ser Asn Gly Lys Leu Arg Val
     50                  55                  60

aac cag gac ggt ttc tac tac ctg tac gct aac atc tgt ttc aac aac      240
Asn Gln Asp Gly Phe Tyr Tyr Leu Tyr Ala Asn Ile Cys Phe Asn Asn
 65                  70                  75                  80

ttc acc gtt tct ttc tgg ctg agg gta ccg aaa gtt tct gct tct cac      288
Phe Thr Val Ser Phe Trp Leu Arg Val Pro Lys Val Ser Ala Ser His
                 85                  90                  95

ctg gaa gtt aaa acc tct atc aaa atc cca tct tca cat aac ctg atg      336
Leu Glu Val Lys Thr Ser Ile Lys Ile Pro Ser Ser His Asn Leu Met
            100                 105                 110

aaa ggt ggt tct acc aaa aac tgg tct ggt aac tct gaa ttc cat ttc      384
Lys Gly Gly Ser Thr Lys Asn Trp Ser Gly Asn Ser Glu Phe His Phe
        115                 120                 125

tac tct atc aac gtt ggt ggt ttc ttc aaa ctg aga gct ggt gaa gaa      432
Tyr Ser Ile Asn Val Gly Gly Phe Phe Lys Leu Arg Ala Gly Glu Glu
    130                 135                 140

atc tct atc cag gtt tct aac cct tct ctg ctg gac cca gac cag gac      480
Ile Ser Ile Gln Val Ser Asn Pro Ser Leu Leu Asp Pro Asp Gln Asp
145                 150                 155                 160

gct acc tac ttc ggg gcc ttc aaa gtt cag gac atc gac                  519
Ala Thr Tyr Phe Gly Ala Phe Lys Val Gln Asp Ile Asp
                165                 170


<210> SEQ ID NO 20
<211> LENGTH: 173
<212> TYPE: PRT
<213> ORGANISM: Artificial Sequence
<220> FEATURE:
<223> OTHER INFORMATION: Description of Artificial Sequence: Fusion
      between murine OPGL, residues 158-316 with tetanus toxoid
      P30 epitope introduced, and His tag

<400> SEQUENCE: 20

Met Lys His Gln His Gln His Gln His Gln His Gln His Gln Lys Pro
  1               5                  10                  15

Glu Ala Gln Pro Phe Ala His Leu Thr Ile Asn Ala Ala Ser Ile Pro
             20                  25                  30

Ser Gly Ser His Lys Val Thr Leu Ser Ser Trp Tyr His Asp Arg Gly
         35                  40                  45

Trp Ala Lys Ile Ser Asn Met Thr Leu Ser Asn Gly Lys Leu Arg Val
     50                  55                  60

Asn Gln Asp Gly Phe Tyr Tyr Leu Tyr Ala Asn Ile Cys Phe Asn Asn
 65                  70                  75                  80

Phe Thr Val Ser Phe Trp Leu Arg Val Pro Lys Val Ser Ala Ser His
```

-continued

```
                 85                  90                  95

Leu Glu Val Lys Thr Ser Ile Lys Ile Pro Ser Ser His Asn Leu Met
            100                 105                 110

Lys Gly Gly Ser Thr Lys Asn Trp Ser Gly Asn Ser Glu Phe His Phe
        115                 120                 125

Tyr Ser Ile Asn Val Gly Gly Phe Phe Lys Leu Arg Ala Gly Glu Glu
    130                 135                 140

Ile Ser Ile Gln Val Ser Asn Pro Ser Leu Leu Asp Pro Asp Gln Asp
145                 150                 155                 160

Ala Thr Tyr Phe Gly Ala Phe Lys Val Gln Asp Ile Asp
                165                 170


<210> SEQ ID NO 21
<211> LENGTH: 68
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 21

agctgcaggt agtcggttgg aacagaacca gaggtttcgt gatgtctgaa acagatgtta     60

gcgtacag                                                              68


<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 22

ctcatctgac catcaacgct gcat                                            24


<210> SEQ ID NO 23
<211> LENGTH: 64
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 23

tttcggtacc ctcagccaga aagaaacggt gaagttgttg aaacagatgt tagcgtacag     60

gtag                                                                  64


<210> SEQ ID NO 24
<211> LENGTH: 61
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 24

tgagggtacc gaaagtttct gcttctcacc tggaagttaa aacccctatc aaaatccaat     60

c                                                                     61


<210> SEQ ID NO 25
<211> LENGTH: 63
<212> TYPE: DNA
```

-continued

<213> ORGANISM: Artificial Sequence
<220> FEATURE:
<223> OTHER INFORMATION: Description of Artificial Sequence: Synthetic
PCR primer

<400> SEQUENCE: 25
tttcggtacc ctcagccaga aagaaacggt gaagttgttg aacatcaggt tatgtgaaga 60
ttg 63

<210> SEQ ID NO 26
<211> LENGTH: 62
<212> TYPE: DNA
<213> ORGANISM: Artificial Sequence
<220> FEATURE:
<223> OTHER INFORMATION: Description of Artificial Sequence: Synthetic
PCR primer

<400> SEQUENCE: 26
tgagggtacc gaaagtttct gcttctcacc tggaaaactg gtctggtaac tctgaattcc 60
at 62

<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
PCR primer

<400> SEQUENCE: 27
tacctgcagc tgatggttta cgttgttaaa acccctatca aaatccaatc ttcacataac 60
ctgatgcagt acatcaaag 79

<210> SEQ ID NO 28
<211> LENGTH: 83
<212> TYPE: DNA
<213> ORGANISM: Artificial Sequence
<220> FEATURE:
<223> OTHER INFORMATION: Description of Artificial Sequence: Synthetic
PCR primer

<400> SEQUENCE: 28
tggaattcag agttaccaga ccagttcagt tcggtgatac cgatgaattt cgaattagct 60
ttgatgtact gcatcaggtt atg 83

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
PCR primer

<400> SEQUENCE: 29
gaatttcgaa ttagctttga tgtactgttc ttcaccagct ctcagtttg 49

<210> SEQ ID NO 30
<211> LENGTH: 53
<212> TYPE: DNA
<213> ORGANISM: Artificial Sequence
<220> FEATURE:
<223> OTHER INFORMATION: Description of Artificial Sequence: Synthetic
PCR primer

<400> SEQUENCE: 30

-continued gctaattcga aattcatcgg tatcaccgaa ctggacgcta cctacttcgg ggc 53

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic PCR primer

<400> SEQUENCE: 31
cttactagtc gatgtcctga actttg 26

<210> SEQ ID NO 32
<211> LENGTH: 74
<212> TYPE: DNA
<213> ORGANISM: Artificial Sequence
<220> FEATURE:
<223> OTHER INFORMATION: Description of Artificial Sequence: Synthetic PCR primer

<400> SEQUENCE: 32
agtggaattc agagttacca gaccagtttt tggtagaacc acctttcatc aggttatgtg 60
aagatgggat tttg 74

<210> SEQ ID NO 33
<211> LENGTH: 65
<212> TYPE: DNA
<213> ORGANISM: Clostridium tetani

<400> SEQUENCE: 33
actacctgca gctgatggtt tacgttgtta aaacctctat caaaatccca tcttcacata 60
acctg 65

<210> SEQ ID NO 34
<211> LENGTH: 15
<212> TYPE: PRT
<213> ORGANISM: Clostridium tetani

<400> SEQUENCE: 34

Gln Tyr Ile Lys Ala Asn Ser Lys Phe Ile Gly Ile Thr Glu Leu
1 5 10 15

<210> SEQ ID NO 35
<211> LENGTH: 21
<212> TYPE: PRT
<213> ORGANISM: Clostridium tetani

<400> SEQUENCE: 35

Phe Asn Asn Phe Thr Val Ser Phe Trp Leu Arg Val Pro Lys Val Ser
1 5 10 15

Ala Ser His Leu Glu
20

<210> SEQ ID NO 36
<211> LENGTH: 13
<212> TYPE: PRT
<213> ORGANISM: Artificial Sequence -continued

```
<220> FEATURE:
<223> OTHER INFORMATION: Pan DR Epitope (PADRE) Peptide

<400> SEQUENCE: 36

Ala Lys Phe Val Ala Ala Trp Thr Leu Lys Ala Ala Ala
1               5                   10
```